US007355084B2

(12) United States Patent
Böttcher et al.

(10) Patent No.: US 7,355,084 B2
(45) Date of Patent: Apr. 8, 2008

(54) METHOD FOR HYDROGENATING ORGANIC COMPOUNDS BY MEANS OF RU/SIO₂ CATALYSTS

(75) Inventors: Arnd Böttcher, Frankenthal (DE); Dominic Vanoppen, Kapellen (BE); Jan-Dirk Arndt, Mannheim (DE); Jochem Henkelmann, Mannheim (DE); Konrad Knoll, Ludwigshafen (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 617 days.

(21) Appl. No.: 10/480,196

(22) PCT Filed: Jun. 7, 2002

(86) PCT No.: PCT/EP02/06287

§ 371 (c)(1),
(2), (4) Date: Dec. 10, 2003

(87) PCT Pub. No.: WO02/100536

PCT Pub. Date: Dec. 19, 2002

(65) Prior Publication Data

US 2004/0199033 A1    Oct. 7, 2004

(30) Foreign Application Priority Data

Jun. 11, 2001    (DE) ................. 101 28 242

(51) Int. Cl.
*C07C 5/00* (2006.01)
(52) U.S. Cl. .............. 585/267; 585/271; 568/821; 564/450; 564/451
(58) Field of Classification Search ............. 585/267, 585/271; 564/450, 451; 568/821
See application file for complete search history.

(56) References Cited

U.S. PATENT DOCUMENTS

| | | | |
|---|---|---|---|
| 2,606,925 A | 8/1952 | Whitmann | |
| 2,822,392 A | 2/1958 | Illich et al. | |
| 2,898,387 A | 8/1959 | Teter | |
| 2,927,127 A | 3/1960 | Sommerville | |
| 3,027,398 A | 3/1962 | Foohey | |
| 3,202,723 A | 8/1965 | Thonon | |
| 3,244,644 A | 4/1966 | Stiles | |
| 3,520,928 A | 7/1970 | Greco | |
| 3,597,489 A | 8/1971 | Dang Vu | |
| 3,636,108 A | 1/1972 | Brake et al. | |
| 3,697,449 A | 10/1972 | Brake et al. | |
| 3,917,540 A | 11/1975 | Pollitzer | |
| 4,882,384 A | 11/1989 | Willis et al. | |
| 4,914,239 A | 4/1990 | Kiyuma | |
| 5,286,898 A | 2/1994 | Gustafson et al. | |
| 5,319,129 A | 6/1994 | Gustafson et al. | |
| 5,334,790 A * | 8/1994 | Richard et al. ............. 585/271 |
| 6,248,924 B1 * | 6/2001 | Ruhl et al. .................. 564/450 |

FOREIGN PATENT DOCUMENTS

| | | |
|---|---|---|
| BE | 739 376 | 9/1969 |
| DE | 805 518 | 3/1951 |
| DE | 2 132 547 | 1/1973 |
| DE | 2 909 663 | 9/1979 |
| DE | 2 823 165 | 11/1979 |
| DE | 3 401 343 | 5/1985 |
| DE | 19624485 A1 * | 1/1998 |
| DE | 19 833 094 | 1/2000 |
| DE | 10 050 709 | 4/2002 |
| DE | 10 050 711 | 4/2002 |
| EP | 0 053 818 | 6/1982 |
| EP | 0 067 058 | 12/1982 |
| EP | 0 141 054 | 7/1984 |
| EP | 0 324 984 | 7/1989 |
| EP | 0 501 265 | 2/1992 |
| EP | 0 603 825 | 6/1994 |
| EP | 0 501 265 | 11/1994 |
| EP | 0 668 257 | 8/1995 |
| EP | 0 803 488 | 10/1997 |
| EP | 0 813 906 | 12/1997 |

(Continued)

OTHER PUBLICATIONS

Hong et al., J. Phys. Chem. 91, 2665-2671 (1987); "*Effect of Silica Support on Ru-Cu Cluster Morphology As Determined by Catalytic Activity*".

(Continued)

*Primary Examiner*—Glenn Caldarola
*Assistant Examiner*—Prem C. Singh
(74) *Attorney, Agent, or Firm*—Novak Druce + Quigg LLP

(57) ABSTRACT

In a process for hydrogenating at least one organic compound, the organic compound or compounds is/are brought into contact with a hydrogen-containing gas in the presence of a catalyst which comprises, as active metal, ruthenium either alone or together with at least one further metal of transition group I, VII or VIII of the Periodic Table applied to a support material based on amorphons silicon dioxide and is obtainable by:

i) a single or multiple treatment of a support material based on amorphous silicon dioxide with a halogen-free aqueous solution of a low molecular weight ruthenium compound and subsequent drying of the treated support material at below 200° C., ii) reduction of the solid obtained in i) by means of hydrogen at from 100 to 350° C., with step ii) being carried out directly after step i).

24 Claims, No Drawings

FOREIGN PATENT DOCUMENTS

| | | |
|---|---|---|
| GB | 799396 | 8/1958 |
| GB | 1104275 | 2/1968 |
| GB | 1144499 | 3/1969 |
| GB | 1155539 | 6/1969 |
| GB | 1341057 | 12/1973 |
| JP | 43-3180 | 2/1943 |
| JP | 47-32532 | 11/1972 |
| JP | 59-196 843 | 11/1984 |
| JP | 7-19901 | 1/1995 |
| PL | 137 526 | 12/1986 |
| WO | WO 94/21694 | 9/1994 |
| WO | WO 96/34896 | 11/1996 |
| WO | WO 99/32427 | 7/1999 |
| WO | WO 00/56783 | 9/2000 |
| WO | WO 00/77054 | 12/2000 |
| WO | WO 00/78704 | 12/2000 |
| WO | WO 01/12681 | 2/2001 |
| WO | WO 01/23437 | 4/2001 |

OTHER PUBLICATIONS

SU 403 658—Abstract, Jan. 21, 1972.
SU 319 582—Abstract, Nov. 5, 1970
JP-Abstract 84-315129/51, 1984.
CA 70/11218, Feb. 5, 1968.

* cited by examiner

METHOD FOR HYDROGENATING ORGANIC COMPOUNDS BY MEANS OF RU/SIO₂ CATALYSTS

The present invention relates to a process for hydrogenating at least one organic compound by bringing the organic compound or compounds into contact with a hydrogen-containing gas in the presence of a catalyst comprising, as active metal, ruthenium either alone or together with at least one further metal of transition group I, VII or VIII of the Periodic Table applied to a support material based on amorphous silicon dioxide.

Various hydrogenation processes are known from the literature. Industrially interesting processes are, in particular, the hydrogenation of substituted or unsubstituted aromatics, phenol derivatives and aniline derivatives, of compounds containing C—C, C—O, N—O and C—N multiple bonds and of polymers.

Cycloaliphatic alcohols, in particular alkylcyclohexanols, are important intermediates for the production of various fragrances, drugs and other organic fine chemicals.

Cycloaliphatic amines, in particular substituted or unsubstituted cyclohexylamines and dicyclohexylamines, are used for preparing aging inhibitors for rubbers and plastics, as corrosion inhibitors and as intermediates for crop protection agents and textile assistants. In addition, cycloaliphatic diamines are used in the production of polyamide and polyurethane resins and are also used as hardeners for epoxy resins.

Hydrogenation products of benzopolycarboxylic acids or derivatives thereof are used, for example, as plasticizers for polymers.

Processes for the catalytic hydrogenation of these classes of compounds are also known.

There are numerous processes for the hydrogenation of benzene to cyclohexane. These hydrogenations are predominantly carried out in the gas or liquid phase over nickel and platinum catalysts (cf., for example, U.S. Pat. Nos. 3,597,489, 2,898,387 and GB 799 396). Typically, the major part of the benzene is firstly hydrogenated to cyclohexane in a main reactor and the conversion into cyclohexane is subsequently completed in one or more after-reactors.

The strongly exothermic hydrogenation reaction requires careful temperature and residence time control in order to achieve complete conversion at high selectivity. In particular, significant formation of methylcyclopentane, which occurs preferentially at relatively high temperatures, has to be suppressed. Typical cyclohexane specifications require a residual benzene content of <100 ppm and a methylcyclopentane content of <200 ppm. The n-paraffin content (n-hexane, n-pentane, etc.) is also critical. These undesirable compounds are likewise preferentially formed at relatively high hydrogenation temperatures and can, like methylcyclopentane, only be separated from the cyclohexane product by means of complicated separation operations (extraction, rectification or, as described in GB 1 341 057, use of molecular sieves). The catalyst used for the hydrogenation also has a strong influence on the extent to which the undesirable methylcyclopentane is formed.

In view of this background, it is desirable to carry out the hydrogenation at the lowest possible temperatures. However, this is limited by the fact that a hydrogenation activity of the catalyst which is sufficiently high to obtain economical space-time yields is, depending on the type of hydrogenation catalyst used, attained only at relatively high temperatures.

Nickel and platinum catalysts used for the hydrogenation of benzene have a series of disadvantages. Nickel catalysts are very sensitive to sulfur-containing impurities in the benzene, so that it is either necessary to use very pure benzene for the hydrogenation or, as described in GB 1 104 275, a platinum catalyst which tolerates a higher sulfur content is used in the main reactor so as to protect the after-reactor which is charged with a nickel catalyst. Another possibility is doping the catalyst with rhenium (GB 1 155 539) or producing the catalyst using ion exchangers (GB 1 144 499). However, the production of such catalysts is complicated and expensive. The hydrogenation can also be carried out over Raney nickel (U.S. Pat. No. 3,202,723), but a disadvantage is the ready combustibility of this catalyst. Homogeneous nickel catalysts can also be used for the hydrogenation (EP-A 0 668 257). However, these catalysts are very water-sensitive, so that the benzene used firstly has to be dried to a residual water content of <1 ppm in a drying column prior to the hydrogenation. A further disadvantage of the homogeneous catalyst is that it cannot be regenerated.

Platinum catalysts have fewer disadvantages than nickel catalysts, but are much more expensive to produce. When using both platinum and nickel catalysts, very high hydrogenation temperatures are necessary, which can lead to significant formation of undesirable by-products.

The patent literature also reports the use of ruthenium-containing catalysts for this application:

SU 319582 uses suspended Ru catalysts doped with Pd, Pt or Rh for the preparation of cyclohexane from benzene. However, the catalysts are made very expensive by the use of Pd, Pt or Rh. Furthermore, the work-up and recovery of the catalyst is complicated and expensive in the case of suspended catalysts.

In SU 403658, a Cr-doped Ru catalyst is used for preparing cyclohexane. However, the hydrogenation is carried out at 180° C., at which a significant amount of undesirable by-product is generated.

U.S. Pat. No. 3,917,540 claims $Al_2O_3$-supported catalysts for preparing cyclohexane. These comprise, as active metal, a noble metal from transition group VIII of the Periodic Table, and also an alkali metal and technetium or rhenium. However, the hydrogenation of benzene can be carried out over such catalysts with a selectivity of only 99.5%.

Finally, U.S. Pat. No. 3,244,644 describes ruthenium hydrogenation catalysts supported on $\eta$-$Al_2O_3$ which are said to be suitable for, inter alia, the hydrogenation of benzene. However, these catalysts contain at least 5% of active metal, and the preparation of $\eta$-$Al_2O_3$ is complicated and expensive.

PCT/EP 00/03326 describes a process for hydrogenating substituted or unsubstituted aromatics in the presence of a catalyst comprising, as active metal, at least one metal of transition group VIII of the Periodic Table applied to a macroporous support. DE 100 50 709.3 describes a process for hydrogenating alkyl-substituted monocyclic or polycyclic aromatics in the presence of a catalyst comprising an active metal of transition group VIII on a monolithic support.

The hydrogenation of alkylphenols to form the corresponding alkylcyclohexanols in the presence of hydrogenation catalysts, in particular supported catalysts, has likewise been described many times.

Examples of catalysts used are metallic rhodium, rhodium-platinum alloys, rhodium-ruthenium alloys and ruthenium, palladium or nickel on catalyst supports. Catalyst supports used are carbon, barium carbonate and, in particular, aluminum oxide.

Thus, for example, DE 100 50 711.5 relates to a process for the hydrogenation of alkyl-, OH— and $NH_2$-substituted aromatics by means of reactive distillation. The hydrogenation is carried out by means of reactive distillation in a reaction column with the reactants being passed in countercurrent over the catalyst(s) fixed in the reaction column.

PL 137 526 describes the hydrogenation of p-tert-butylphenol to form p-tert-butylcyclohexanol using a nickel catalyst.

DE-A-34 01 343 and EP 0 141 054 describe a process for preparing 2- and 4-tert-butylcyclohexanol from 2- and 4-tert-butylphenol by catalytic hydrogenation. The hydrogenation is carried out in two stages, using a palladium catalyst on an Al203 support in the first stage and a ruthenium catalyst on an $Al_2O_3$ support in the second stage. The metal content on the support is from 0.1 to 5% by weight. Supports are not specified in more detail. The hydrogenation is carried out at a pressure of 300 bar with recirculation of product, and from 0.1 to 0.5% of by-products are formed.

U.S. Pat. No. 2,927,127 describes a process for preparing p-tert-butylcyclohexanol and esters thereof by catalytic hydrogenation of p-tert-butylphenol. Catalysts used are 5% rhodium on carbon, 5% palladium on barium carbonate and 5% ruthenium on carbon. When using ruthenium on carbon, the hydrogenation was carried out at a pressure of from 70 to 120 bar and a temperature of from 74 to 93° C. 66% cis isomer were obtained as hydrogenation product.

DE-A-29 09 663 describes a process for preparing cis-alkylcyclohexanols by catalytic hydrogenation of the corresponding alkylphenols. Ruthenium on an $Al_2O_3$ support was used as catalyst. The hydrogenation was carried out at a pressure of 40, 60 or 80 bar. The product obtained consisted predominantly of cis-alkylcyclohexanols, with from 0.1 to 1% of alkylbenzenes being obtained as by-product.

Correspondingly, the hydrogenation of aromatic amines to cycloaliphatic amines in the presence of hydrogenation catalysts, in particular catalysts applied to supports, is also known.

Catalysts used are, for example, Raney cobalt with basic additives (JP 43/3180), nickel catalysts (U.S. Pat. No. 4,914,239, DE 80 55 18), rhodium catalysts (BE 73 93 76, JP 70 19 901, JP 72 35 424) and palladium catalysts (U.S. Pat. No. 3,520,928, EP 501 265, EP 53 818, JP 59/196 843). However, the majority of catalysts used are ruthenium-containing catalysts.

DE 21 32 547 discloses a process for hydrogenating monocyclic or polycyclic aromatic diamines in the presence of a suspended ruthenium catalyst to form the corresponding cycloaliphatic amines.

EP 67 058 describes a process for preparing cyclohexylamine by catalytic hydrogenation of the corresponding aromatic amine. As catalyst, use is made of ruthenium metal in finely divided form on activated aluminum pellets. After being recycled four times, the catalyst started to lose its effectiveness.

EP 324 984 relates to a process for preparing a mixture of substituted or unsubstituted cyclohexylamine and substituted or unsubstituted dicyclohexylamine by hydrogenation of substituted or unsubstituted aniline using a catalyst which comprises ruthenium and palladium on a support and, in addition, an alkaline alkali metal compound as modifier. A process which is similar in principle is described in EP 501 265, where the catalyst contains niobic acid, tantalic acid or a mixture of the two as modifier.

U.S. Pat. No. 2,606,925 describes a process for preparing an aminocyclohexyl compound by hydrogenation of a corresponding aromatic compound using a ruthenium catalyst whose active catalytic component is selected from among elemental ruthenium, ruthenium oxides, ruthenium salts in which the ruthenium is present in the anion or in the cation. As the examples of this process show, the catalyst there is also prepared in a separate step and dried and introduced into the reaction vessel after a relatively long drying time.

A further process for preparing cyclohexylamine is described in U.S. Pat. No. 2,822,392, in which the main focus is on the use of a specific reactor in which the aniline and the hydrogen as starting materials are reacted with one another in countercurrent.

U.S. Pat. No. 3,636,108 and U.S. Pat. No. 3,697,449 relate to the catalytic hydrogenation of aromatic, nitrogen-containing compounds using a ruthenium catalyst which further comprises an alkali metal compound as modifier.

EP-A 0 803 488 and EP-A 0 813 906 describe processes for the reaction of organic compounds in the presence of a supported ruthenium catalyst. Particular mention is made of the hydrogenation of aromatic compounds containing hydroxyl and amino groups. The catalyst described in EP-A 0 813 906 is a catalyst comprising, as active metal, ruthenium alone or together with at least one metal of transition group I, VII or VIII of the Periodic Table applied to a support, where the support has a mean pore diameter of at least 50 nm and a BET surface area of not more than 30 $m^2/g$ and the amount of active metal is from 0.01 to 30% by weight, based on the total weight of the catalyst and the ratio of the surface area of the active metal to that of the catalyst support is <0.05.

Disadvantages which have been found, particularly in hydrogenation using a rhodium-containing catalyst, are not only the high price of the catalyst but also the fact that these reactions not infrequently result in the formation of relatively large amounts of alkylbenzenes and further compounds which cannot be identified and are formed as decomposition products or by-products in the hydrogenation. These by-products make the work-up and purification of the reaction product more difficult, particularly when, for example, alkylcyclohexanols are to be used as fragrances or for the preparation of fragrances. Furthermore, the activity of many of the catalysts used in the above-described processes drops rapidly, especially when the hydrogenation is carried out at relatively high reaction temperatures to accelerate the reaction rate.

Processes for the hydrogenation of polymers comprising at least one unit capable of hydrogenation are also known per se.

For example, WO 94/21694 describes the hydrogenation of polystyrene or styrene-butadiene or styrene-isoprene block copolymers over supported metal catalysts. Under the reaction conditions, not only the diene block but also the phenyl groups of the polystyrene block are hydrogenated. In this way, the polystyrene block is converted into a polyvinylcyclohexyl block (PVCH).

DE 198 33 094 describes hydrogenations of aromatic polymers. Catalysts described are, in particular, ones having a specific pore structure. However, these are complicated to produce.

An improved hydrogenation catalyst for the ring hydrogenation of styrene polymers is described in WO 96/34896. Starting materials described there for the ring hydrogenation are polystyrene and also styrene-diene block copolymers such as S—B, S—I, S—B—S and S—I—S. Furthermore, the hydrogenation of styrene-butadiene or styrene-isoprene block copolymers having 3 or 5 blocks (WO 00/77054, WO 00/56783, WO 01/12681) and the hydrogenation of star-shaped styrene-butadiene block copolymers (WO 01/23437) have also been described. U.S. Pat. No. 4,882,384 describes the ring hydrogenation of linear S—B, S—B—S and star-shaped (S—B)$_n$.

A further industrially important process is the hydrogenation of benzenepolycarboxylic acids to form the corresponding cyclohexane derivatives.

In U.S. Pat. Nos. 5,286,898 and 5,319,129, dimethyl terephthalate is hydrogenated at $\geq 140°$ C. and a pressure of from 50 to 170 bar over supported Pd catalysts admixed with Ni, Pt and/or Ru to form the corresponding dimethyl hexahydroterephthalate. In DE-A 28 23 165, aromatic carboxylic esters are hydrogenated at from 70 to 250° C. and from 30 to 200 bar over supported Ni, Ru, Rh and/or Pd catalysts to form the corresponding cycloaliphatic carboxylic esters. U.S. Pat. No. 3,027,398 describes the hydrogenation of dimethyl terephthalate at from 110 to 140° C. and from 35 to 105 bar over supported Ru catalysts.

EP-A 0 603 825 relates to a process for preparing 1,4-cyclohexanedicarboxylic acid by hydrogenation of terephthalic acid using a supported palladium catalyst in which the support is aluminum oxide, silicon dioxide or activated carbon. A particular aspect of the process described there is that the 1,4-cyclohexanedicarboxylic acid solution obtained in a first step is brought into contact with steam and the impurities present in the solution are thereby extracted. However, this process is applicable only to acids, since there is a risk of hydrolysis when it is applied to derivatives such as esters, anhydrides, etc.

The patent application WO 99/32427 discloses a process for hydrogenating benzenepolycarboxylic acid or derivatives thereof, e.g. esters and/or anhydrides, by bringing one or more benzenepolycarboxylic acids or one or more derivatives thereof into contact with a hydrogen-containing gas in the presence of a macroporous catalyst. In PCT/EP 00/05351, mention is made, in particular, of the hydrogenation of isophthalic acid and terephthalic acid.

It is an object of the present invention to provide an inexpensive process by means of which various organic compounds can be hydrogenated with high selectivity and in a high space-time yield.

We have found that this object is achieved by a process for hydrogenating at least one organic compound by bringing the organic compound or compounds into contact with a hydrogen-containing gas in the presence of a catalyst comprising, as active metal, ruthenium either alone or together with at least one further metal of transition group I, VII or VIII of the Periodic Table applied to a support material based on amorphous silicon dioxide. The ruthenium catalyst is obtainable by:

i) a single or multiple treatment of a support material based on amorphous silicon dioxide with a halogen-free aqueous solution of a low molecular weight ruthenium compound and subsequent drying of the treated support material at below 200° C., ii) reduction of the solid obtained in i) by means of hydrogen at from 100 to 350° C., with step ii) being carried out directly after step i).

For the purposes of the present invention, the term "organic compound" encompasses all organic compounds which are capable of catalytic hydrogenation. It encompasses both low molecular weight organic compounds and polymers. Here, "low molecular weight organic compounds" are compounds having a molecular weight of up to 500 g/mol. The term "polymer" refers to molecules having a molecular weight of more than about 500 g/mol or molecules having more than two repeating units.

It is possible to use, in particular, organic compounds which contain one or more of the following structural units: C—C double bonds, C—C triple bonds, aromatic groups, C—N double bonds, C—N triple bonds, C—O double bonds, N—O double bonds, C—S double bonds, NO$_2$ groups, where the functional groups may also be present in polymers or cyclic structures, for example in unsaturated heterocycles.

The process of the present invention can also be used to react organic compounds comprising units of various structures as defined above, e.g. organic compounds containing both C—C multiple bonds and carbonyl groups. According to the present invention, it is possible for only one or a plurality of the hydrogenatable units of various structures to be hydrogenated.

The process of the present invention has the particular advantage that the catalyst used is versatile. The catalyst is inexpensive to prepare and thus leads to a process which is more favorable overall. The hydrogenation products can be prepared with high selectivity and in a high space-time yield by means of the process of the present invention, so that complicated purification steps are unnecessary. Furthermore, the catalyst used according to the present invention has a high operating life.

Industrially important hydrogenations are, for example, the hydrogenations of unsubstituted and alkyl-substituted monocyclic or polycyclic aromatic compounds. These can easily be hydrogenated to form the corresponding cyclic alkanes by means of the process of the present invention.

The present invention therefore provides, in one embodiment, a process for hydrogenating at least one organic compound by bringing the organic compound or compounds into contact with a hydrogen-containing gas in the presence of a catalyst comprising, as active metal, ruthenium either alone or together with at least one further metal of transition group I, VII or VIII of the Periodic Table applied to a support material based on amorphous silicon dioxide, wherein the organic compound is an unsubstituted monocyclic or polycyclic aromatic or a monocyclic or polycyclic aromatic substituted by at least one alkyl group.

In the process of the present invention, it is in principle possible to use all monocyclic or polycyclic aromatics which are either unsubstituted or bear one or more alkyl groups, either individually or as mixtures of two or more thereof, preferably individually. The length of the alkyl groups is subject to no particular restrictions, but the alkyl groups generally contain from 1 to 30, preferably from 1 to 18, in particular from 1 to 4, carbon atoms. Specific examples of starting materials for the present process are, in particular, the following aromatics:

Benzene, toluene, xylenes, cumene, diphenylmethane, tribenzenes, tetrabenzenes, pentabenzenes and hexabenzenes, triphenylmethane, alkyl-substituted naphthalenes, naphthalene, alkyl-substituted anthracenes, anthracene, alkyl-substituted tetralins and tetralin. The present process is preferably used for hydrogenating benzene to cyclohexane.

The present invention accordingly provides, in a preferred embodiment, a process for hydrogenating a monocyclic or polycyclic aromatic selected from among benzene, toluene, xylenes, cumene, diphenylmethane, tribenzenes, tetrabenzenes, pentabenzenes and hexabenzenes, triphenylmethane, alkyl-substituted naphthalenes, naphthalene, alkyl-substituted anthracenes, anthracene, alkyl-substituted tetralins and tetralin.

In a further preferred embodiment, the present invention provides a process in which benzene is converted into cyclohexane.

However, it is also possible according to the present invention to hydrogenate heteroaromatic or heterocyclic unsaturated compounds.

The term "heteroaromatic and heterocyclic unsaturated compound" used for the purposes of the present invention encompasses all cyclic compounds containing at least one heteroatom, i.e. all compounds which contain at least one nitrogen, phosphorus, oxygen or sulfur atom and are also unsaturated. The term "heteroaromatic" encompasses aromatic compounds having a heteroatom in the aromatic ring system. The term "heterocyclic unsaturated" in this context encompasses cyclic compounds which have isolated or conjugated double bonds. Owing to the selective hydrogenation capability of the catalyst used here, the compounds to be hydrogenated can also contain further functional groups which are in principle hydrogenatable or reducible, e.g. —CHO, —CH$_2$OH, —COOH, —COOR (R=alkyl), —CH$_2$COOH, —CH$_2$COOR (R=alkyl). It is of course also possible to hydrogenate compounds of the abovementioned type which are substituted by groups which cannot be reduced, e.g. alkylpyridines.

The compounds used in each case can then be reacted selectively to form the corresponding ring-hydrogenated compounds.

Specific mention may be made of the following compounds or classes of compound: pyridines, pyrans, thiopyrans, picolins, pyrroles, furans, thiophenes, indoles, pyrazoles, imidazoles, azepines, thiazoles and pyrazines.

In particular, the following reactions are carried out by the present process:

ring hydrogenation of pyrroles to form the corresponding tetrahydropyrroles (pyrrolidines);
hydrogenation of quinoline to form decahydroquinoline;
conversion of isoquinoline into decahydroisoquinoline;
conversion of indole into octahydroindole;
conversion of isoindole into octahydroisoindole;
conversion of acridine into tetradecahydroacridine;
conversion of pyridine into piperidine;
conversion of furan into tetrahydrofuran;
conversion of nicotinic acid, picolinic acid or isonicotinic acid into the corresponding ring-hydrogenated derivatives.

It is likewise possible, within the scope of the present invention, to use substituted monocyclic or polycyclic aromatic compounds which have unsaturated substituents on the aromatic ring or in a side chain in the hydrogenation. It is also possible according to the present invention to control the hydrogenation so that only the aromatic or both the aromatic and the unsaturated group are hydrogenated.

According to the present invention, it is also possible to hydrogenate compounds which contain further functional groups. For example, it is possible, according to the present invention, to hydrogenate organic compounds in which at least one hydroxyl group is bound to an aromatic ring. As in the case of compounds in which at least one hydroxyl group is bound to an aromatic ring, it is also possible in the process of the present invention to hydrogenate aromatic compounds in which at least one amino group is bound to an aromatic ring with high selectivity to form the corresponding cycloaliphatic compounds.

The present invention therefore also provides, in a further embodiment, a process for hydrogenating at least one organic compound by bringing the organic compound or compounds into contact with a hydrogen-containing gas in the presence of a catalyst comprising, as active metal, ruthenium either alone or together with at least one further metal of transition group I, VII or VIII of the Periodic Table applied to a support material based on amorphous silicon dioxide, wherein the organic compound is an aromatic compound in which at least one hydroxyl group or at least one amino group is bound to an aromatic ring.

The monocyclic or polycyclic aromatic compounds containing at least one hydroxyl group or amino group are preferably hydrogenated in the presence of the catalyst described herein to form the corresponding cycloaliphatic compounds in which the hydroxyl group or the amino group is retained. In particular, the formation of deamination products, for example cyclohexanes, or partially hydrogenated dimerization products such as phenylcyclohexylamines in the hydrogenation of aromatic amines is virtually completely avoided in this embodiment.

The process of the present invention can therefore also be used, in particular, to hydrogenate aromatic compounds which contain not only at least one hydroxyl group or at least one amino group but also at least one substituted or unsubstituted $C_1$-$C_{10}$-alkyl group bound to an aromatic ring or at least one $C_1$-$C_{10}$-alkoxy group bound to an aromatic ring.

The present invention therefore also provides, in a preferred embodiment, a process for hydrogenating an aromatic compound which contains at least one substituted or unsubstituted $C_1$-$C_{10}$-alkyl group bound to an aromatic ring or at least one $C_1$-$C_{10}$-alkoxy group bound to an aromatic ring in addition to at least one hydroxyl group or at least one amino group.

If aromatic compounds in which at least one hydroxyl group or at least one amino group and, in addition, at least one substituted or unsubstituted $C_{1-10}$-alkyl radical and/or -alkoxy radical are bound to an aromatic ring are used in the process of the present invention, the resulting isomer ratio of cis- to trans-configured products can be varied within a wide range as a function of the reaction conditions (temperature, solvent). Furthermore, the compounds obtained can be processed further without additional purification steps. The formation of alkylbenzenes is virtually completely avoided.

The process of the present invention enables aromatic compounds in which at least one hydroxyl group and preferably also at least one substituted or unsubstituted $C_{1-10}$-alkyl radical and/or -alkoxy radical is/are bound to an aromatic ring to be hydrogenated to form the corresponding cycloaliphatic compounds. It is in this case also possible to use mixtures of two or more of these compounds. The aromatic compounds may be monocyclic or polycyclic aromatic compounds. The aromatic compounds contain at least one hydroxyl group bound to an aromatic ring; the simplest compound of this type is phenol. The aromatic compounds preferably have one hydroxyl group per aromatic ring. The aromatic compounds can be substituted on the aromatic ring or rings by one or more alkyl and/or alkoxy radicals, preferably $C_{1-10}$-alkyl or -alkoxy radicals, particularly preferably $C_{1-10}$-alkyl radicals, in particular methyl, ethyl, propyl, isopropyl, butyl, isobutyl, tert-butyl radicals; among the alkoxy radicals, preference is given to $C_{1-8}$-alkoxy radicals such as methoxy, ethoxy, propoxy, isopropoxy, butoxy, isobutoxy, tert-butoxy radicals. The aromatic ring or rings and the alkyl and alkoxy radicals may be substituted by halogen atoms, in particular fluorine atoms, or bear other suitable inert substituents.

The compounds which can be reacted according to the present invention, preferably hydrogenated, preferably bear from one to four $C_1$-$C_{10}$-alkyl radicals, in particular one $C_{1-10}$-alkyl radical which is preferably located on the same aromatic ring as the hydroxyl group or groups. Preferred compounds are (mono)alkylphenols in which the alkyl radical can be located in the o, m or p position relative to the hydroxyl group. Particular preference is given to para-alkylphenols, also referred to as 4-alkylphenols, in which the alkyl radical preferably has from 1 to 10 carbon atoms and in particular is a tert-butyl radical. Preference is given to 4-tert-butylphenol. Polycyclic aromatic compounds which can be used according to the present invention are, for example, α-naphthol and β-naphthol.

The aromatic compounds in which at least one hydroxyl group and preferably also at least one substituted or unsubstituted $C_{1-10}$-alkyl radical and/or -alkoxy radical are bound to an aromatic ring can also have a plurality of aromatic rings which are linked via an alkylene radical, preferably a methylene group. The linking alkylene group, preferably methylene group, can bear one or more alkyl substituents which may be $C_{1-20}$-alkyl radicals and are preferably $C_{1-10}$-alkyl radicals, particularly preferably methyl, ethyl, propyl, isopropyl, butyl or tert-butyl radicals.

In this case, each of the aromatic rings can bear at least one hydroxyl group. Examples of such compounds are bisphenols which are linked in the 4 position via an alkylene radical, preferably a methylene radical.

In the process of the present invention, particular preference is given to reacting a phenol substituted by a $C_{1-10}$-alkyl radical, preferably $C_{1-6}$-alkyl radical, which may be substituted by an aromatic radical, or mixtures of two or more of these compounds.

In a further preferred embodiment of this process, p-tert-butylphenol, bisphenol A, 2,6-dimethylphenol or methylphenol, e.g. p-methylphenol is reacted.

The process of the present invention also enables aromatic compounds in which at least one amino group is bound to an aromatic ring to be reacted, preferably hydrogenated to the corresponding cycloaliphatic compounds, with it also being possible to use mixtures of two or more of these compounds. The aromatic compounds can be monocyclic or polycyclic aromatic compounds. The aromatic compounds contain at least one amino group bound to an aromatic ring. The aromatic compounds are preferably aromatic amines or diamines. The aromatic compounds can be substituted on the aromatic ring or rings or on the amino group by one or more alkyl and/or alkoxy radicals, preferably $C_{1-10}$-alkyl radicals, in particular methyl, ethyl, propyl, isopropyl, butyl, isobutyl, tert-butyl radicals; among the alkoxy radicals, preference is given to $C_{1-10}$-alkoxy radicals such as methoxy, ethoxy, propoxy, isopropoxy, butoxy, isobutoxy, tert-butoxy radicals. The aromatic ring or rings and the alkyl and alkoxy radicals may be substituted by halogen atoms, in particular fluorine atoms, or bear other suitable inert substituents.

The aromatic compound in which at least one amino group is bound to an aromatic ring can also have a plurality of aromatic rings which are linked via an alkylene group, preferably a methylene group. The linking alkylene group, preferably methylene group, can bear one or more alkyl substituents which may be $C_{1-20}$-alkyl radicals and are preferably $C_{1-10}$-alkyl radicals, particularly preferably methyl, ethyl, propyl, isopropyl, butyl, sec-butyl or tert-butyl radicals.

The amino group bound to the aromatic ring can likewise be substituted by one or two of the above-described alkyl radicals.

Particularly preferred compounds are aniline, toluenediamine, naphthylamine, diaminobenzenes, diaminotoluenes and bis-p-aminophenylmethane or mixtures thereof.

The present invention therefore provides, in a preferred embodiment, a process in which aniline is hydrogenated to cyclohexylamine.

In a further preferred embodiment, the present invention provides a process in which p-tert-butylphenol, bisphenol A, 2,6-dimethylphenol or p-methylphenol is hydrogenated.

According to the present invention, it is also possible to hydrogenate organic compounds which contain C—C, C—O, N—O or C—N multiple bonds.

The present invention therefore also provides, in a further preferred embodiment, a process for hydrogenating at least one organic compound by bringing the organic compound or compounds into contact with a hydrogen-containing gas in the presence of a catalyst comprising, as active metal, ruthenium either alone or together with at least one further metal of transition group I, VII or VIII of the Periodic Table applied to a support material based on amorphous silicon dioxide, wherein the organic compound contains at least one C—C, C—O, N—O or C—N multiple bond.

In particular, the present invention makes it possible to hydrogenate organic compounds which contain a multiple bond, for example a C—C double or triple bond, a C—N double or triple bond or a C—O double bond. For the purposes of the present invention, particular preference is given to aldehyde, ketones, nitriles, alkynes, alkynols, alkenes, imines, carboxylic acids, carboxylic esters and heterocyclic unsaturated compounds.

The present invention therefore provides, in a preferred embodiment, a process in which the organic compound having at least one multiple bond is selected from the group consisting of aldehydes, ketones, nitriles, alkynes, alkynols, alkenes, imines, carboxylic acids, carboxylic esters and heterocyclic unsaturated compounds.

The process of the present invention enables compounds containing C=O groups, i.e. in particular, aldehydes, ketones, carboxylic acids and their derivatives such as carboxylic esters, carboxylic acid halides and carboxylic anhydrides, and unsaturated heterocycles and mixtures of two or more of the abovementioned compounds to be hydrogenated.

Here, particular preference is given to using aldehydes and ketones, preferably those having from 1 to 20 carbon atoms, e.g. formaldehyde, acetaldehyde, propionaldehyde, n-butyraldehyde, valeraldehyde, caproaldehyde, heptaldehyde, phenylacetaldehyde, acrolein, crotonaldehyde, benzaldehyde, o-tolualdehyde, m-tolualdehyde, p-tolualdehyde, salicylaldehyde, anisaldehyde, vanillin, cimmamaldehyde, acetone, methyl ethyl ketone, 2-pentanone, 3-pentanone, 2-hexanone, 3-hexanone, cyclohexanone, isophorone, methyl isobutyl ketone, mesityl oxide, acetophenone, propiophenone, benzophenone, benzalacetone, dibenzalacetone, benzalacetophenone, glycolaldehyde, glyceraldehyde, glyoxal, 2,3-butanedione, 2,4-pentanedione, 2,5-hexanedione, terephthalaldehyde, glutaraldehyde, diethyl ketone, methyl vinyl ketone, acetylacetone, 2-ethylhexanal or mixtures of two or more thereof.

It is also possible to hydrogenate carboxylic acids and derivatives thereof, with preference being given to those having from 1 to 20 carbon atoms. Specific examples are:

carboxylic acids such as formic acid, acetic acid, propionic acid, butyric acid, isobutyric acid, n-valeric acid, trimethylacetic acid (pivalic acid), caproic acid, enanthic acid, caprylic acid, capric acid, lauric acid, myristic acid, palmitic acid, stearic acid, acrylic acid, methacrylic acid, oleic acid, elaidic acid, linoleic acid, linolenic acid, cyclohexanecarboxylic acid, benzoic acid, phenylacetic acid, o-toluic acid, m-toluic acid, p-toluic acid, o-chlorobenzoic acid, p-chlorobenzoic acid, o-nitrobenzoic acid, p-nitrobenzoic acid, salicylic acid, p-hydroxybenzoic acid, anthranilic acid, p-aminobenzoic acid, oxalic acid, malonic acid, succinic acid, glutaric acid, adipic acid, pimelic acid, suberic acid, azelaic acid, sebacic acid, maleic acid, fumaric acid, phthalic acid, isophthalic acid, terephthalic acid;

carboxylic esters such as the $C_1$-$C_{10}$-alkyl esters of the abovementioned carboxylic acids, in particular methyl formate, ethyl acetate, butyl butyrate, dimethyl terephthalate, dimethyl adipate, methyl (meth)acrylate, butyrolactone, caprolactone and polycarboxylic esters such as polyacrylic and polymethacrylic esters and their copolymers and polyesters, e.g. polymethyl methacrylate;

carboxylic anhydrides, e.g. the anhydrides of the abovementioned carboxylic acids, in particular acetic anhydride, propionic anhydride, benzoic anhydride and maleic anhydride;

carboxamides such as formamide, acetamide, propionamide, stearamide, terephthalamide.

It is also possible to react hydroxycarboxylic acids such as lactic, malic, tartaric or citric acid, or amino acids such as glycine, alanine, proline and arginine.

Furthermore, it is also possible to react nitriles, preferably aliphatic and aromatic mononitriles and dinitriles, e.g. acetonitrile, propionitrile, butyronitrile, dimethyl-aminopropionitrile, stearonitrile, isocrotononitrile, 3-butenenitrile, propynenitrile, 3-butinenitrile, 2,3-butadienenitrile, 2,4-pentadienenitrile, 3-hexene-1,6-dinitrile, chloroacetonitrile, trichloroacetonitrile, lactonitrile, phenylacetonitrile, 2-chloro-benzonitrile, 2,6-dichlorobenzonitrile, isophthalonitrile and terephthalonitrile, in particular aliphatic α,ωdinitriles, e.g. succinonitrile, glutaronitrile, adiponitrile, pimelonitrile and suberonitrile, or aminonitriles such as 4-aminobutanenitrile, 5-aminopentanenitrile, 6-aminohexanenitrile, 7-aminoheptanenitrile and 8-aminooctanenitrile.

The process of the present invention can also be used for carrying out the hydrogenation of imines such as quinonimines, ketimines, ketenimines or aliphatic imines, e.g. propanimine, hexanimine.

The process of the present invention can in principle also be used for hydrogenating all polymers which have hydrogenatable groups, in particular those which have at least one C—C double bond, at least one aromatic group or at least one carbonyl group or at least one C—N triple bond. For the purposes of the present invention, particular preference is given to the hydrogenation of polymers containing C—C double bonds or aromatic groups.

The present invention therefore also provides, in a further embodiment, a process for hydrogenating at least one organic compound by bringing the organic compound or compounds into contact with a hydrogen-containing gas in the presence of a catalyst comprising, as active metal, ruthenium either alone or together with at least one further metal of transition group I, VII or VIII of the Periodic Table applied to a support material based on amorphous silicon dioxide, wherein the organic compound is a polymer containing at least one C—C double bond, at least one aromatic group or at least one carbonyl group or at least one C—N triple bond.

In particular, the process of the invention makes it possible to hydrogenate styrene-butadiene and styrene-isoprene block copolymers to form polymers having a variety of properties, for example improved aging or weathering resistance. Depending on the hydrogenation conditions, the olefinic double bonds or both the olefinic double bonds and the aromatic double bonds can be hydrogenated selectively.

The present invention therefore provides, in a preferred embodiment, a process in which Polystyrene, a butadiene copolymer or an isoprene copolymer is hydrogenated.

It is also possible for polymers having C—C double bonds, e.g. polybutadienes such as poly(2,3-dimethylbutadiene), polyisoprene, polyacetylenes and polycyclopentadienes and polycyclohexadienes; polymers having C—C triple bonds, e.g. polydiacetylenes; and polymers containing aromatic groups, e.g. polystyrene, acrylonitrile-butadiene-styrene terpolymers and styrene-acrylonitrile copolymers to be hydrogenated according to the present invention.

Apart from polystyrene, it is possible, in particular, to hydrogenate block copolymers of vinylaromatic monomers and dienes according to the present invention. Vinylaromatic monomers which can be used are, for example, styrene, alpha-methylstyrene, ring-alkylated styrenes such as p-methylstyrene or tert-butylstyrene, or 1,1-diphenylethylene or mixtures thereof.

Preferred dienes are butadiene, isoprene, 2,3-dimethylbutadiene, 1,3-pentadiene, 1,3-hexadiene or piperylene or mixtures thereof, particularly preferably butadiene and isoprene.

Apart from the blocks S of vinylaromatic monomers, the block copolymers before the hydrogenation can also have a pure diene block B or a copolymer block S/B made up of vinylaromatic monomers and dienes. The copolymer block can have a random distribution of monomers or a monomer gradient.

The block copolymers can have a linear or star-shaped structure. The molecular weight $M_n$ of the total block copolymer is generally in the range from 50 000 to 300 000 g per mol, preferably in the range from 80 000 to 250 000 g per mol.

Preference is given to linear block copolymers having the structures S—B—S/B—S, $S_1$—B—S/B—$S_2$, $S_1$13 B—$S_2$, S1-(S/B)$_1$—(S/B)$_2$—S and $S_1$—(S/B)—B—$S_2$. Preference is likewise given to the star-shaped structures $S_1$—B—X—B—$S_2$, $S_1$—(S/B)—B—X—B—(S/B)—$S_2$ and $S_1$—(S/B)$_1$—(S/B)$_2$—X—(S/B)$_2$—(S/B)$_1$—$S_2$, where S is a vinylaromatic polymer block, B is a diene block, S/B is a copolymer block made up of vinylaromatic monomers and diene, X is an oligofunctional coupling unit.

Further polymers which can be hydrogenated according to the present invention are described in DE 101 24 254.9, whose relevant contents are fully incorporated by reference into the present application.

Further examples of starting materials suitable for the process of the present invention are styrene-butadiene block copolymers whose butadiene units have already been pre-hydrogenated (e.g. Kraton G from Shell).

According to the present invention, it is possible, in particular, for the hydrogenation to directly follow the polymerization. If the polymer has been obtained by solution polymerization, the polymer-containing solution which results can be used directly for the reaction in the process of the present invention.

The present invention therefore provides a process in which the hydrogenation is carried out in a process step which directly follows the polymerization for preparing the polymer.

The process of the present invention is also particularly useful for the reaction, preferably hydrogenation, of polymers comprising units of various structures as defined above, e.g. polymers which contain both C—C multiple bonds and C═O groups and/or C≡N groups, since the catalysts used in the process of the present invention are able to selectively react firstly the C—C multiple bonds, i.e. achieve a conversion of these groups of from about 90 to 100%, while the C=O and/or C≡N groups are initially hydrogenated to an extent of less than 25%, generally to an extent of from 0 to about 7%.

After hydrogenation of the C—C multiple bonds present in the polymers is complete, it is of course possible to hydrogenate the remaining unsaturated groups present in the polymer, e.g. C=O groups, virtually quantitatively by further introduction of hydrogen.

The process of the present invention can be used both for polymers which have been isolated and for living polymers.

A further important class of compounds which can be hydrogenated by means of the process of the present invention are benzenepolycarboxylic acids or derivatives thereof. Hydrogenation according to the present invention makes it possible to obtain alkyl cyclohexanedicarboxylates which can be used, for example, as plasticizers.

The present invention therefore also provides, in a further embodiment, a process for hydrogenating at least one organic compound by bringing the organic compound or compounds into contact with a hydrogen-containing gas in the presence of a catalyst comprising, as active metal, ruthenium either alone or together with at least one further metal of transition group I, VII or VIII of the Periodic Table applied to a support material based on amorphous silicon dioxide, wherein the organic compound is a benzenepolycarboxylic acid or a derivative thereof or a mixture of two or more thereof.

The term "benzenepolycarboxylic acids or derivatives thereof" encompasses both the respective benzenepolycarboxylic acids themselves and derivatives thereof, in particular monoesters, diesters, triesters or tetraesters and anhydrides of the benzenepolycarboxylic acids. The esters used are alkyl, cycloalkyl or alkoxyalkyl esters in which the alkyl, cycloalkyl and alkoxyalkyl groups generally have from 1 to 30, preferably from 2 to 20 and particularly preferably from 3 to 18, carbon atoms and may be branched or linear. Mixed esters of benzenepolycarboxylic acids can also be used for the purposes of the present invention.

Specific examples are:

alkyl terephthalates such as monomethyl terephthalate, dimethyl terephthalate, diethyl terephthalate, di-n-propyl terephthalate, di-n-butyl terephthalate, di-tert-butyl terephthalate, diisobutyl terephthalate, the monoglycol ester of terephthalic acid, the diglycol ester of terephthalic acid, di-n-octyl terephthalate, diisooctyl terephthalate, mono-2-ethylhexyl terephthalate, di-2-ethylhexyl terephthalate, di-n-nonyl terephthalate, diisononyl terephthalate, di-n-decyl terephthalate, di-n-undecyl terephthalate, diisodecyl terephthalate, diisododecyl terephthalate, di-n-octadecyl terephthalate, diisooctadecyl terephthalate, di-n-eicosyl terephthalate, monocyclohexyl terephthalate, dicyclohexyl terephthalate;

alkyl phthalates such as monomethyl phthalate, dimethyl phthalate, diethyl phthalate, di-n-propyl phthalate, di-n-butyl phthalate, di-tert-butyl phthalate, diisobutyl phthalate, the monoglycol ester of phthalic acid, the diglycol ester of phthalic acid, di-n-octyl phthalate, diisooctyl phthalate, di-2-ethylhexyl phthalate, di-n-nonyl phthalate, diisononyl phthalate, di-n-decyl phthalate, diisodecyl phthalate, di-n-undecyl phthalate, diisododecyl phthalate, di-n-octadecyl phthalate, diisooctadecyl phthalate, di-n-eicosyl phthalate, monocyclohexyl phthalate, dicyclohexyl phthalate;

alkyl isophthalates such as monomethyl isophthalate, dimethyl isophthalate, diethyl isophthalate, di-n-propyl isophthalate, di-n-butyl isophthalate, di-tert-butyl isophthalate, diisobutyl isophthalate, the monoglycol ester of isophthalic acid, the diglycol ester of isophthalic acid, di-n-octyl isophthalate, diisooctyl isophthalate, di-2-ethylhexyl isophthalate, di-n-nonyl isophthalate, diisononyl isophthalate, di-n-decyl isophthalate, diisodecyl isophthalate, di-n-undecyl isophthalate, diisododecyl isophthalate, di-n-octadecyl isophthalate, diisooctadecyl isophthalate, di-n-eicosyl isophthalate, monocyclohexyl isophthalate, dicyclohexyl isophthalate;

alkyl trimellitates such as monomethyl trimellitate, dimethyl trimellitate, diethyl trimellitate, di-n-propyl trimellitate, di-n-butyl trimellitate, di-tert-butyl trimellitate, diisobutyl trimellitate, the monoglycol ester of trimellitic acid, the diglycol ester of trimellitic acid, di-n-octyl trimellitate, diisooctyl trimellitate, di-2-ethylhexyl trimellitate, di-n-nonyl trimellitate, diisononyl trimellitate, di-n-decyl trimellitate, diisodecyl trimellitate, di-n-undecyl trimellitate, diisododecyl trimellitate, di-n-octadecyl trimellitate, diisooctadecyl trimellitate, di-n-eicosyl trimellitate, monocyclohexyl trimellitate, dicyclohexyl trimellitate and also trimethyl trimellitate, triethyl trimellitate, tri-n-propyl trimellitate, tri-n-butyl trimellitate, tri-tert-butyl trimellitate, triisobutyl trimellitate, the triglycol ester of trimellitic acid, tri-n-octyl trimellitate, triisooctyl trimellitate, tri-2-ethylhexyl trimellitate, tri-n-nonyl trimellitate, triisododecyl trimellitate, tri-n-undecyl trimellitate, triisododecyl trimellitate, tri-n-octadecyl trimellitate, triisooctadecyl trimellitate, tri-n-eicosyl trimellitate, tricyclohexyl trimellitate;

alkyl trimesates such as monomethyl trimesate, dimethyl trimesate, diethyl trimesate, di-n-propyl trimesate, di-n-butyl trimesate, di-tert-butyl trimesate, diisobutyl trimesate, the monoglycol ester of trimesic acid, the diglycol ester of trimesic acid, di-n-octyl trimesate, diisooctyl trimesate, di-2-ethylhexyl trimesate, di-n-nonyl trimesate, diisononyl trimesate, di-n-decyl trimesate, diisodecyl trimesate, di-n-undecyl trimesate, diisododecyl trimesate, di-n-octadecyl trimesate, diisooctadecyl trimesate, di-n-eicosyl trimesate, monocyclohexyl trimesate, dicyclohexyl trimesate and also trimethyl trimesate, triethyl trimesate, tri-n-propyl trimesate, tri-n-butyl trimesate, tri-tert-butyl trimesate, triisobutyl trimesate, the triglycol ester of trimesic acid, tri-n-octyl trimesate, triisooctyl trimesate, tri-2-ethylhexyl trimesate, tri-n-nonyl trimesate, triisododecyl trimesate, tri-n-undecyl trimesate, triisododecyl trimesate, tri-n-octadecyl trimesate, triisooctadecyl trimesate, tri-n-eicosyl trimesate, tricyclohexyl trimesate;

alkyl hemimellitates such as monomethyl hemimellitate, dimethyl hemimellitate, diethyl hemimellitate, di-n-propyl hemimellitate, di-n-butyl hemimellitate, di-tert-butyl hemimellitate, diisobutyl hemimellitate, the monoglycol ester of hemimellitic acid, the diglycol ester of hemimellitic acid, di-n-octyl hemimellitate, diisooctyl hemimellitate, di-2-ethylhexyl hemimellitate, di-n-nonyl hemimellitate, diisononyl hemimellitate, di-n-decyl hemimellitate, diisodecyl hemimellitate, di-n-undecyl hernimellitate, diisododecyl hemimellitate, di-n-octadecyl hemimellitate, diisooctadecyl hernimellitate, di-n-eicosyl hernimellitate, monocyclohexyl hemimellitate, dicyclohexyl hemimellitate and also trimethyl hemimellitate, triethyl hemimellitate, tri-n-propyl hemimellitate, tri-n-butyl hemimellitate, tri-tert-butyl hemimellitate, triisobutyl hemimellitate, the triglycol ester of hemimellitic acid, tri-n-octyl hemimellitate, triisooctyl hemimellitate, tri-2-ethylhexyl hemimellitate, tri-n-nonyl hemimellitate, triisododecyl hemimellitate, tri-n-undecyl hemimellitate, triisododecyl hemimellitate, tri-n-octadecyl hemimellitate, triisooctadecyl hemimellitate, tri-n-eicosyl hemimellitate, tricyclohexyl hemimellitate;

alkyl pyromellitates such as monomethyl pyromellitate, dimethyl pyromellitate, diethyl pyromellitate, di-n-propyl pyromellitate, di-n-butyl pyromellitate, di-tert-butyl pyromellitate, diisobutyl pyromellitate, the monoglycol ester of pyromellitic acid, the diglycol ester of pyromellitic acid, di-n-octyl pyromellitate, diisooctyl pyromellitate, di-2-ethylhexyl pyromellitate, di-n-nonyl pyromellitate, diisononyl pyromellitate, di-n-decyl pyromellitate, diisodecyl pyromellitate, di-n-undecyl pyromellitate, diisododecyl pyromellitate, di-n-octadecyl pyromellitate, diisooctadecyl pyromellitate, di-n-eicosyl pyromellitate, monocyclohexyl pyromellitate, trimethyl pyromellitate, triethyl pyromellitate, tri-n-propyl pyromellitate, tri-n-butyl pyromellitate, tri-tert-butyl pyromellitate, triisobutyl pyromellitate, the triglycol ester of pyromellitic acid, tri-n-octyl pyromellitate, triisooctyl pyromellitate, tri-2-ethylhexyl pyromellitate, tri-n-nonyl pyromellitate, triisododecyl pyromellitate, tri-n-undecyl pyromellitate, triisododecyl pyromellitate, tri-n-octadecyl pyromellitate, triisooctadecyl pyromellitate, tri-n-eicosyl pyromellitate, tricyclohexyl pyromellitate, and also tetramethyl pyromellitate, tetraethyl pyromellitate, tetra-n-propyl pyromellitate, tetra-n-butyl pyromellitate, tetra-tert-butyl pyromellitate, tetraisobutyl pyromellitate, the tetraglycol ester of pyromellitic acid, tetra-n-octyl pyromellitate, tetraisooctyl pyromellitate, tetra-2-ethylhexyl pyromellitate, tetra-n-nonyl pyromellitate, tetraisododecyl pyromellitate, tetra-n-undecyl pyromellitate, tetraisododecyl pyromellitate, tetra-n-octadecyl pyromellitate, tetraisooctadecyl pyromellitate, tetra-n-eicosyl pyromellitate, tetracyclohexyl pyromellitate;

anhydrides of phthalic acid, trimellitic acid, hemimellitic acid and pyromellitic acid.

It is of course also possible to use mixtures of two or more of these compounds.

The benzenepolycarboxylic acid or the derivative thereof is preferably selected from the group consisting of: di(isopentyl) phthalate having the Chemical Abstracts Registry Number (hereinafter: CAS No.) 84777-06-0; di(isoheptyl) phthalate having the CAS No. 71888-89-6; di(isononyl) phthalate having the CAS No. 68515-48-0; di(isononyl) phthalate having the CAS No. 28553-12-0, based on n-butene; di(isononyl) phthalate having the CAS No. 28553-12-0, based on isobutene; di(nonyl) phthalate having the CAS No. 68515-46-8; di(isodecyl) phthalate having the CAS No. 68515-49-1; 1,2-di-$C_{7-11}$ phthalate having the CAS No. 68515-42-4; di-$C_{7-11}$ phthalates having the following CAS No.: 111 381-89-6, 111 381 90-9, 111 381 91-0, 68515-44-6, 68515-45-7 and 3648-20-7; di-$C_{9-11}$ phthalate having the CAS No. 98515-43-5; di(isodecyl) phthalate consisting mainly of di(2-propylheptyl) phthalate; the phthalic ester containing branched or linear $C_{7-9}$-alkyl ester groups; examples of corresponding phthalates which can be used as starting materials have the following CAS No.: di-$C_{7-9}$ alkyl phthalate having the CAS No. 111 381-89-6; di-$C_7$-alkyl phthalate having the CAS No. 68515-44-6; and di-$C_9$-alkyl phthalate having the CAS No. 68515-45-7.

Also preferred are benzenepolycarboxylic esters selected from among the commercially available benzenecarboxylic esters having the trade names Jayflex DINP (CAS No. 68515-48-0), Jayflex DIDP (CAS No. 68515-49-1), Palatinol 9-P, Vestinol 9 (CAS No. 28553-12-0), TOTM-I (CAS No. 3319-31-1), Linplast 68-TM, Palatinol N (CAS No. 28553-12-0), Jayflex DHP (CAS No. 68515-50-4), Jayflex DIOP (CAS No. 27554-26-3), Jayflex UDP (CAS No. 68515-47-9), Jayflex DIUP (CAS No. 85507-79-5), Jayflex DTDP (CAS No. 68515-47-9), Jayflex L9P (CAS No. 68515-45-7), Jayflex L911P (CAS No. 68515-43-5), Jayflex L11P (CAS No. 3648-20-2), Witamol 110 (CAS No. 90193-91-2), Witamol 118 (di-n-$C_8$-$C_{10}$-alkyl phthalate), Unimoll BB (CAS No. 85-68-7), Linplast 1012 BP (CAS No. 90193-92-3), Linplast 13 XP (CAS No. 27253-26-5), Linplast 610 P (CAS No. 68515-51-5), Linplast 68 FP (CAS No. 68648-93-1) and Linplast 812 HP (CAS No. 70693-30-0), Palatinol AH (CAS No. 117-81-7), Palatinol 711 (CAS No. 68515-42-4), Palatinol 911 (CAS No. 68515-43-5), Palatinol 11 (CAS No. 3648-20-2), Palatinol Z (CAS No. 26761-40-0) and Palatinol DIPP (CAS No. 84777-06-0).

The products obtained according to the present invention are in these cases always the corresponding cyclohexanepolycarboxylic acids or cyclohexanepolycarboxylic acid derivatives. According to the present invention, both cis and trans isomers can be obtained.

The present invention accordingly provides, in a preferred embodiment, a process for hydrogenating a benzenepolycarboxylic acid or a derivative thereof selected from the group consisting of monoalkyl and dialkyl esters of phthalic acid, terephthalic acid and isophthalic acid, monoalkyl, dialkyl and trialkyl esters of trimellitic acid, trimesic acid and hemimellitic acid, monoalkyl, dialkyl, trialkyl and tetraalkyl esters of pyromellitic acid, where the alkyl groups may be linear or branched and each have from 3 to 18 carbon atoms, anhydrides of phthalic acid, trimellitic acid and hemimellitic acid, pyromellitic dianhydride and mixtures of two or more thereof.

The process of the present invention is carried out using a catalyst comprising, as active metal, ruthenium either alone or together with at least one further metal of transition group I, VII or VIII of the Periodic Table applied to a support material based on amorphous silicon dioxide. This catalyst is obtainable by:

i) a single or multiple treatment of a support material based on amorphous silicon dioxide with a halogen-free aqueous solution of a low molecular weight ruthenium compound and subsequent drying of the treated support material at below 200° C., ii) reduction of the solid obtained in i) by means of hydrogen at from 100 to 350° C., with step ii) being carried out directly after step i).

For the purposes of the present invention, the term "directly" means, in particular, that the drying step i) according to the present invention is followed without intermediate calcination by step ii), i.e. the reduction according to the present invention.

In the following, the implementation of the present invention is described using ruthenium alone as active metal. However, analogous procedures can be employed when ruthenium is used together with at least one further metal of transition group I, VII or VIII of the Periodic Table.

In the catalysts obtainable as described above, the ruthenium is distributed particularly well over the surface of the support material. The ruthenium is present as metallic ruthenium in the catalysts used according to the present invention as a result of the way in which the catalyst is prepared. The ruthenium is present on the support material in atomically dispersed form and/or in the form of ruthenium particles which are present virtually exclusively, i.e. to an extent of more than 90%, preferably more than 95%, based on the number of visible particles, as isolated particles having diameters below 10 nm, in particular below 7 nm. In other words, the catalyst contains essentially no, i.e. to an extent of less than 10%, in particular less than 5%, ruthenium particles and/or agglomerates of ruthenium particles having diameters above 10 nm. As a result of the use of halogen-free ruthenium precursors and solvents in the preparation, the chlorine content of the catalysts used according to the present invention is below 0.05% by weight, based on the total weight of the catalyst.

An essential aspect of this catalyst is the use of a support material based on amorphous silicon dioxide. In this context, the term "amorphous" means that the proportion of crystalline silicon dioxide phases is less than 10% of the support material. The support materials used for preparing the catalyst employed according to the present invention can, however, have long-range structures which are formed by regular arrangement of pores in the support material.

Possible support materials are in principle all amorphous silicon dioxide types which comprise at least 90% by weight of silicon dioxide, with the remaining 10% by weight, preferably not more than 5% by weight, of the support material being able to be another oxidic material, e.g. MgO, CaO, $TiO_2$, $ZrO_2$, $Fe_2O_3$ or alkali metal oxide. It goes without saying that the support material used is likewise free of halogen, i.e. the halogen content is preferably less than 500 ppm. The support material preferably contains not more than 1% by weight, particularly preferably not more than 0.5% by weight and in particular no detectable amounts, of aluminum oxide, calculated as $Al_2O_3$. In a preferred embodiment, support materials containing less than 500 ppm of $Fe_2O_3$ are used. The proportion of alkali metal oxide generally results from the preparation of the support material and can be up to 2% by weight. It is frequently less than 1% by weight. Supports which are free of alkali metal oxide (<0.1% by weight) are also suitable. The proportion of MgO, CaO, $TiO_2$ and $ZrO_2$ can be up to 10% by weight of the support material, but is preferably not more than 5% by weight. Support materials containing no detectable amounts of these metal oxides (<0.1% by weight) are also suitable.

Preference is given to support materials having a specific surface area in the range from 50 to 700 $m^2/g$, in particular in the range from 80 to 600 $m^2/g$ and especially in the range from 100 to 600 $m^2/g$ (BET surface area in accordance with DIN 66131). Pulverulent support materials preferably have a specific surface area in the range from 200 to 600 $m^2/g$ and shaped bodies preferably have a specific surface area in the range from 200 to 300 $m^2/g$.

Suitable amorphous support materials based on silicon dioxide are well known to those skilled in the art and are commercially available (cf., for example, O. W. Flörke, "Silica" in Ullmann's Encyclopedia of Industrial Chemistry 5th ed. on CD-ROM). They can be either of natural origin or can have been produced synthetically. Examples of suitable amorphous support materials based on silicon dioxide are kieselguhr, silica gels, pyrogenic silica and precipitated silica. In a preferred embodiment of the invention, the catalysts comprise silica gels as support materials.

Depending on the way in which the hydrogenation process of the present invention is carried out, the support material can have different forms. If the process is carried out as a suspension process, the support material is usually used in the form of a finely divided powder for preparing the catalyst. When the catalyst is used in fixed beds, use is usually made of shaped bodies of the support material which are obtainable, for example, by screw extrusion, ram extrusion or tableting and can have, for example, the shape of spheres, tablets, cylinders, rods, rings or hollow cylinders, stars and the like. The dimensions of the shaped bodies are usually in the range from 1 mm to 25 mm. Use is frequently made of catalyst extrudates having diameters of from 2 to 5 mm and lengths of from 2 to 25 mm.

In a preferred embodiment, the present invention therefore provides a process for hydrogenating at least one organic compound using a catalyst which has at least one of the following properties:

(1) the support based on amorphous silicon dioxide has a BET surface area in the range from 50 to 700 $m^2/g$;
(2) the catalyst comprises ruthenium, either alone or together with at least one further metal of transition group I, VII or VIII of the Periodic Table, in an amount of from 0.2 to 10% by weight, based on the weight of the support;
(3) the support material based on silicon dioxide comprises at least 90% by weight of silicon dioxide and less than 1% by weight of aluminum oxide, calculated as $Al_2O_3$.

In a further preferred embodiment, the present invention therefore provides a process for hydrogenating at least one organic compound using a catalyst which contains less than 0.05% by weight of halogen, based on the total weight of the catalyst, and comprises:

a support material based on amorphous silicon dioxide and elemental ruthenium, either alone or together with at least one further metal of transition group I, VII or VIII of the Periodic Table as metal, which is present on the support in atomically dispersed form or in the form of metal particles or in atomically dispersed form and in the form of metal particles, where the catalyst contains essentially no metal particles or agglomerates having diameters above 10 nm.

In a further preferred embodiment, the present invention provides a process in which the ruthenium catalyst is regenerated.

Suitable methods of regenerating the ruthenium catalyst are, for example, treatment with halogen-free acid as described in U.S. Pat. No. 4,072,628, treatment with aqueous hydrogen peroxide or other halogen-free oxidizing agents or regeneration by means of oxygen as described, for example, in BE 882 279.

In the following, the catalyst used according to the present invention is described in more detail, with the descriptions being based on ruthenium alone as active metal. However, the details apply analogously to the use of ruthenium together with at least one further metal of transition group I, VII or VIII of the Periodic Table.

The ruthenium content of the catalyst can be varied over a wide range. It is generally at least 0.1% by weight, preferably at least 0.2% by weight, and frequently does not exceed 10% by weight, in each case based on the weight of the support material. The ruthenium content is preferably in the range from 0.2 to 7% by weight, in particular in the range from 0.4 to 5% by weight.

To prepare the ruthenium catalysts used according to the present invention, the support material is firstly treated with a halogen-free aqueous solution of a low molecular weight ruthenium compound, hereinafter referred to as (ruthenium) precursor, in such a way that the desired amount of ruthenium is taken up by the support material. This step will hereinafter also be referred to as impregnation. The support which has been treated in this way is subsequently dried at the abovementioned temperatures. If appropriate, the solid obtained in this way is then treated again with the aqueous solution of the ruthenium precursor and dried again. This procedure is repeated until the amount of ruthenium compound taken up by the support material corresponds to the desired ruthenium content of the catalyst.

The treatment or impregnation of the support material can be carried out in various ways and depends in a known manner on the form of the support material. For example, the precursor solution can be sprayed or passed over the support material or the support material can be suspended in the precursor solution. For example, the support material can be suspended in the aqueous solution of the ruthenium precursor and, after a particular time, filtered off from the aqueous supernatant liquid. The ruthenium content of the catalyst can be controlled in a simple manner via the amount of liquid taken up and the ruthenium concentration of the solution. Impregnation of the support material can also, for example, be carried out by treating the support with a defined amount of the aqueous solution of the ruthenium precursor corresponding to the maximum amount of liquid which can be taken up by the support material. For this purpose, the support material can, for example, be sprayed with the liquid. Suitable apparatuses for the impregnation of the support are those customarily used for combining liquids and solids (cf., for example, Vauck, Müller "Grundoperationen chemischer Verfahrenstechnik", 10th edition, Deutscher Verlag für. Kunststoffindustrie, Leipzig, 1994, p. 405 ff.). Examples of suitable apparatuses are tumble dryers, impregnation drums, drum mixers, blade mixers and the like. Monolithic supports are usually impregnated by passing the aqueous solutions of the ruthenium precursor over them.

The aqueous solutions used for the impregnation are, according to the present invention, halogen-free, i.e. they contain no halogen or less than 500 ppm of halogen. The ruthenium precursors used are therefore exclusively ruthenium compounds which contain no chemically bound halogen and are sufficiently soluble in the aqueous solvent. These include, for example, ruthenium(III) nitrosyl nitrate ($Ru(NO)(NO_3)_3$), ruthenium(III) acetate and the alkali metal ruthenate(IV), e.g. sodium and potassium ruthenate(IV).

In the present context, the term "aqueous" refers to water and mixtures of water with up to 50% by volume, preferably not more than 30% by volume and in particular not more than 10% by volume, of one or more organic solvents which are miscible with water, e.g. mixtures of water with $C_1$-$C_4$-alkanols such as methanol, ethanol, n-propanol or isopropanol. Water is frequently used as only solvent. The aqueous solvent will frequently further comprise, for example, a halogen-free acid, e.g. nitric acid, sulfuric acid or acetic acid, to stabilize the ruthenium precursor in the solution. The concentration of the ruthenium precursor in the aqueous solutions naturally depends on the amount of ruthenium precursor to be applied and the absorption capacity of the support material for the aqueous solution and is generally in the range from 0.1 to 20% by weight.

Drying can be carried out at the abovementioned temperatures by the customary methods of drying solids. Adherence to the upper limit specified according to the present invention for the drying temperatures is important for the quality, i.e. the activity, of the catalyst. If the drying temperatures specified above are exceeded, a significant drop in the activity results. Calcination of the support at higher temperatures, e.g. above 300° C. or even 400° C., as proposed in the prior art is not only superfluous but has an adverse effect on the activity of the catalyst.

Drying of the solid impregnated with the ruthenium precursor is usually carried out at atmospheric pressure, although a subatmospheric pressure can also be employed to promote drying. A stream of gas, e.g. air or nitrogen, is frequently passed over or through the material to be dried so as to promote drying.

The drying time naturally depends on the desired degree of drying and the drying temperature and is generally in the range from 2 hours to 30 hours, preferably in the range from 4 to 15 hours.

The treated support material is preferably dried until the content of water or of volatile solvent constituents prior to the reduction ii) is less than 5% by weight, in particular not more than 2% by weight and particularly preferably not more than 1% by weight, based on the total weight of the solid. The proportions by weight indicated are based on the weight loss of the solid determined at 300° C. under a pressure of 1 bar over a period of 10 minutes. The activity of the catalysts used according to the present invention can be increased further in this way.

The solid which has been treated with the precursor solution is preferably kept in motion during drying, for example by drying the solid in a rotary tube oven or a rotary sphere oven. The activity of the catalysts used according to the present invention can be increased further in this way.

Conversion of the solid obtained after drying into its catalytically active form is carried out according to the present invention by hydrogenation of the solid at the abovementioned temperatures in a manner known per se.

For this purpose, the support material is brought into contact at the abovementioned temperatures with hydrogen or a mixture of hydrogen and an inert gas. The hydrogen partial pressure is of minor importance to the result of the reduction and can be varied within a range from 0.2 bar to 1.5 bar. The hydrogenation of the catalyst material is frequently carried out in a stream of hydrogen under a hydrogen pressure of 1 bar. The hydrogenation is preferably carried out with the solid obtained in i) being kept in motion, for example by carrying out the hydrogenation of the solid in a rotary tube oven or a rotary sphere oven. The activity of the catalysts used according to the present invention can be increased further in this way.

After the hydrogenation, the catalyst can be passivated in a known manner, e.g. by briefly treating the catalyst with an oxygen-containing gas, e.g. air but preferably an inert gas mixture containing from 1 to 10% by volume of oxygen, to make it easier to handle.

In a preferred embodiment of the present invention, ruthenium alone is used as active metal.

The catalysts used according to the present invention are suitable as catalysts for the hydrogenation of many organic compounds.

According to the present invention, the hydrogenation can be carried out in the presence of a solvent. However, the hydrogenation in the process of the present invention can also be carried out in the absence of a solvent or diluent, i.e. it is not necessary for the reaction to be carried out in solution.

Particularly for the reaction of polymers, the hydrogenation is preferably carried out in a saturated hydrocarbon in which the polymer is soluble as solvent. Preference is given to cycloaliphatic hydrocarbons, in particular cyclohexane. It is advantageous to use the same solvent as in the polymerization, so that the hydrogenation can be carried out in a process step following the polymerization.

In the case of the hydrogenation of an aromatic compound in which at least one hydroxyl group is bound to an aromatic ring, examples of suitable solvents or diluents include the following: straight-chain or cyclic ethers, for example tetrahydrofuran or dioxane, and aliphatic alcohols in which the alkyl radical preferably has from 1 to 10 carbon atoms, in particular from 3 to 6 carbon atoms. Examples of preferred alcohols are i-propanol, n-butanol, i-butanol and n-hexanol.

Mixtures of these or other solvents or diluents can likewise be used.

In the case of the hydrogenation of an aromatic compound in which at least one amino group is bound to an aromatic ring, examples of suitable solvents or diluents include the following: straight-chain or cyclic ethers, for example tetrahydrofuran or dioxane, and also ammonia and monoalkylamines or dialkylamines in which the alkyl radical preferably has from 1 to 3 carbon atoms, e.g. methylamine, ethylamine, propylamine and the corresponding dialkylamines.

Mixtures of these or other solvents or diluents can likewise be used.

In both the above embodiments, the amount of solvent or diluent used is not restricted in any particular way and can be chosen freely depending on requirements, but preference is given to amounts which lead to a 10-70% strength by weight solution of the compound to be hydrogenated.

For the purposes of the process of the present invention, particular preference is given to using the product formed in the hydrogenation as solvent, if desired together with other solvents or diluents. In this case, part of the product formed in the process can be mixed with the compounds to be hydrogenated. The aromatic compounds to be hydrogenated are preferably mixed with from 1 to 30 times, particularly preferably from 5 to 20 times, in particular from 5 to 10 times, their weight of reaction product as solvent or diluent.

In the case of the other compounds which can be reacted according to the present invention, what has been said above also applies, again without there being any restrictions in respect of the solvents and diluents.

The hydrogenation is carried out at suitable pressures and temperatures. Preference is given to pressures above 1 bar. For example, the hydrogenation can be carried out at pressures of from 1 to 350 bar, in particular from 10 to 300 bar, particularly preferably from 20 to 250 bar. The hydrogenation of, in particular, an unsubstituted monocyclic or polycyclic aromatic or a monocyclic or polycyclic aromatic substituted by at least one alkyl group can advantageously be carried out at pressures of from 10 to 50 bar.

Preferred temperatures are in a range from about 50, in particular about 70, to about 250° C. The hydrogenation of an unsubstituted monocyclic or polycyclic aromatic or a monocyclic or polycyclic aromatic substituted by at least one alkyl group is preferably carried out at from about 75 to about 200° C., in particular from about 75° C. to about 180° C., particularly preferably from 130° C. to 160° C. The hydrogenation of an aromatic compound in which at least one hydroxyl group or at least one amino group is bound to an aromatic ring and the hydrogenation of organic compounds containing at least one C—C, C—O, N—O or C—N multiple bond are carried out at from about 100 to about 220° C., the hydrogenation of polymers is carried out at from about 120 to about 220° C., in particular from about 150° C. to about 200° C., and the hydrogenation of benzenepolycarboxylic acids or derivatives thereof is carried out at from about 50 to about 200° C., in particular from about 70° C. to about 180° C.

In a preferred embodiment, the present invention accordingly provides a process in which the hydrogenation is carried out at from 50 to 250° C.

The hydrogenation process can be carried out continuously or batchwise. According to the present invention, preference is given to a continuous process, especially in a fixed-bed reactor.

The present invention therefore provides, in a preferred embodiment, a process in which the hydrogenation is carried out continuously.

In a continuous process, the amount of compound or compounds to be hydrogenated is preferably from about 0.05 to about 3 kg per liter of catalyst per hour, more preferably from about 0.2 to about 2 kg per liter of catalyst per hour, in particular from about 0.1 to about 1.5 kg per liter of catalyst per hour.

The hydrogenation can be carried out in the gas phase or the liquid phase.

As hydrogenation gases, it is possible to use any gases which comprise free hydrogen and contain no harmful amounts of catalyst poisons such as CO. For example, it is possible to use the offgas from a reformer. Preference is given to using pure hydrogen as hydrogenation gas.

In the case of phenols and amines which are additionally substituted by at least one substituted or unsubstituted $C_{1-10}$-alkyl and/or -alkoxy radical or in the case of the benzenepolycarboxylic acids or derivatives thereof, the isomer ratio of cis- to trans-configured products can be varied within a wide range as a function of the reaction conditions (temperature, solvent).

If an aromatic compound in which at least one amino group is bound to an aromatic ring is to be hydrogenated by means of the catalyst used according to the present invention, the hydrogenation can also be carried out in the presence of ammonia or amines, e.g. dialkylamines, for example methylamine, ethylamine, propylamine or dimethylamine, diethylamine or dipropylamine. In such cases, use is made of appropriate amounts of ammonia or monoalkylamine or dialkylamine, preferably from about 0.5 to about 50 parts by weight, particularly preferably from about 1 to about 20 parts by weight, in each case based on 100 parts by weight of the compound or compounds to be hydrogenated. Particular preference is given to using anhydrous ammonia or anhydrous amines.

The invention is illustrated below by means of some examples, with examples 1 to 8 being examples of the hydrogenation of an unsubstituted monocyclic or polycyclic aromatic or a monocyclic or polycyclic aromatic substituted by at least one alkyl group. Examples 9 to 15 relate to the hydrogenation of an aromatic compound in which at least one hydroxyl group or at least one amino group is bound to an aromatic ring. Examples 16 to 22 relate to the reaction of organic compounds containing at least one C—C, C—O, N—O or C—N multiple bond, while examples 23 and 27 relate to the hydrogenation of polymers and example 28 is an example of the hydrogenation of benzenepolycarboxylic acids or derivatives thereof. Example 29 illustrates the preparation of the catalyst.

EXAMPLES

Example 1

2 g of catalyst A (3% $Ru/SiO_2$) were placed in a 300 ml pressure reactor. The reactor was subsequently charged with 100 g of benzene. The hydrogenation was carried out at 75° C. and a pressure of 50 bar using pure hydrogen. The hydrogenation was continued until no more hydrogen was taken up and the reactor was subsequently vented. The yield of cyclohexane was 99.99%. Methylcyclopentane could not be detected.

Example 2

2 g of catalyst A (3% Ru/SiO$_2$) were placed in a 300 ml pressure reactor. The reactor was subsequently charged with 100 g of benzene. The hydrogenation was carried out at 75° C. and a pressure of 20 bar using pure hydrogen. The hydrogenation was continued until no more hydrogen was taken up and the reactor was subsequently vented. The yield of cyclohexane was 99.99%. Methylcyclopentane could not be detected.

Example 3

2 g of catalyst A (3% Ru/SiO$_2$) were placed in a 300 ml pressure reactor. The reactor was subsequently charged with 100 g of benzene. The hydrogenation was carried out at 130° C. and a pressure of 20 bar using pure hydrogen. The hydrogenation was continued until no more hydrogen was taken up and the reactor was subsequently vented. The yield of cyclohexane was 99.99%.

Example 4

2 g of catalyst A (3% Ru/SiO$_2$) were placed in a 300 ml pressure reactor. The reactor was subsequently charged with 100 g of benzene. The hydrogenation was carried out at 160° C. and a pressure of 50 bar using pure hydrogen. The hydrogenation was continued until no more hydrogen was taken up and the reactor was subsequently vented. The yield of cyclohexane was 99.99%. Methylcyclopentane could not be detected.

Example 5

An electrically heatable flow-through reactor was charged with 1 kg of catalyst C (5% of Ru on SiO$_2$ extrudates). The hydrogenation of benzene was then commenced at 2×10$^6$ Pa and 85° C. without prior activation. The hydrogenation was carried out continuously in the upflow mode, with part of the hydrogenation product being recirculated via a circulation pump and mixed with the feed upstream of the reactor. In this way, an amount of hydrogenation product corresponding to 10 times the amount of benzene was added as solvent. The amount of benzene fed continuously to the reactor corresponded to a WHSV of 0.6 kg/l×h. The output from the reactor no longer contained any benzene and the yield of cyclohexane was above 99.99% (determined by gas chromatography). Methylcyclopentane was not detected.

Example 6

An electrically heatable flow-through reactor was charged with 1 kg of catalyst C (5% of Ru on SiO$_2$ extrudates). The hydrogenation of benzene was then commenced at 5×10$^6$ Pa and 150° C. without prior activation. The hydrogenation was carried out continuously in the upflow mode, with part of the hydrogenation product being recirculated via a circulation pump and mixed with the feed upstream of the reactor. In this way, an amount of hydrogenation product corresponding to 20 times the amount of benzene was added as solvent. The amount of benzene fed continuously to the reactor corresponded to a WHSV of 1.5 kg/l×h. The output from the reactor no longer contained any benzene and the yield of cyclohexane was above 99.99% (determined by gas chromatography). Methylcyclopentane was not detected.

Example 7

Hydrogenation in the Gas Phase

An oil-heated flow-through reactor (glass) was charged with 100 ml of catalyst C (5% of Ru on SiO$_2$ extrudates). The hydrogenation of benzene was then commenced at atmospheric pressure without prior activation. The benzene was vaporized by means of a prevaporizer (80° C.) and passed continuously together with hydrogen (molar ratio=1:7) through the catalyst bed in a single pass at 100° C. and a WHSV of 0.5 kg/l×h. The output was condensed in a cold trap. The benzene was able to be hydrogenated completely to cyclohexane. Methylcyclopentane was not detected.

Example 8

3 g of catalyst A (3% Ru/SiO$_2$) were placed in a 300 ml pressure reactor. The reactor was subsequently charged with 100 g of pyridine. The hydrogenation was carried out at 180° C. and a pressure of 150 bar using pure hydrogen. The hydrogenation was continued until no more hydrogen was taken up and the reactor was subsequently vented. The conversion of pyridine was 100%. The yield of piperidine was 99.3%.

Example 9

2 g of catalyst A (3% Ru/SiO$_2$) were placed in a 300 ml pressure reactor. The reactor was subsequently charged with 150 ml of a 50% strength by weight solution of 4-tert-butylphenol in THF. The hydrogenation was carried out at 130° C. and a pressure of 200 bar using pure hydrogen. The hydrogenation was continued until no more hydrogen was taken up and the reactor was subsequently vented. After the solvent had been distilled off, the hydrogenation product had the following composition:
  99.9% of cis,trans-4-tert-butylcyclohexanol
  0.1% of tert-butylcyclohexane
The aromatic compound 4-tert-butylphenol was completely reacted in the hydrogenation.

Example 10

2 g of catalyst A (3% Ru/SiO$_2$) were placed in a 300 ml pressure reactor. The reactor was subsequently charged with 150 ml of a 50% strength by weight solution of toluenediamine (mixture of the 2,4 and 2,6 isomers) in THF. The hydrogenation was carried out at 160° C. and a pressure of 200 bar using pure hydrogen. The hydrogenation was continued until no more hydrogen was taken up and the reactor was subsequently vented. After the solvent had been distilled off, the hydrogenation product had the following composition:
  diaminomethylcyclohexane: 99.2%
  monomethylcyclohexane: 1.8%
The aromatic compound toluenediamine was completely reacted in the hydrogenation.

Example 11

2 g of catalyst A (3% Ru/SiO$_2$) were placed in a 300 ml pressure reactor. The reactor was subsequently charged with 150 ml of aniline. The hydrogenation was carried out at 160°

C. and a pressure of 200 bar using pure hydrogen. The hydrogenation was continued until no more hydrogen was taken up and the reactor was subsequently vented. The hydrogenation product had the following composition:

cyclohexylamine: 98.5% dicyclohexylamine: 1.5%

Example 12

2 kg of a solution of 50% by weight of bisphenol A in THF and 40 g of catalyst A (3% Ru/SiO$_2$) were placed in a 3.5 l autoclave. Hydrogenation was subsequently carried out batchwise at 150° C. and 200 bar until no more hydrogen was taken up and the reactor was subsequently vented. The conversion to the desired cycloaliphatic diol isomer mixture was quantitative.

Example 13

An electrically heatable flow-through reactor was charged with 1.2 l of catalyst C (5% of Ru on SiO$_2$ extrudates). The hydrogenation of aniline was then commenced at 200 bar and 160° C. without prior activation. The hydrogenation was carried out continuously in the upflow mode, with part of the hydrogenation product being recirculated via a circulation pump and mixed with the feed upstream of the reactor. In this way, an amount of hydrogenation product corresponding to 10 times the amount of aniline was added as solvent. 200 l of H$_2$/h were vented at the top of the separator. The amount of aniline fed continuously to the reactor corresponded to a WHSV of 0.8 kg/l×h.

Under steady-state reaction conditions, the following product compositions were obtained as a function of the reaction temperatures:

| Temperature (° C.) | CHA[1] (%) | DCHA[2] (%) |
|---|---|---|
| 160 | 99.5 | 0.5 |
| 180 | 97.5 | 2.5 |
| 200 | 96.0 | 4.0 |

[1])CHA = cyclohexylamine;
[2])DCHA = dicyclohexylamine

Example 14

The hydrogenation was carried out as described in example 13, but anhydrous ammonia was also metered in continuously. Based on 100% by weight of aniline, 10 parts by weight of ammonia were added. Under steady-state reaction conditions, the following product compositions were obtained as a function of the reaction temperatures:

| Temperature (° C.) | CHA[1] (%) | DCHA[2] (%) |
|---|---|---|
| 180 | 99.9 | 0.1 |
| 200 | 99.0 | 1.0 |

[1])CHA = cyclohexylamine;
[2])DCHA = dicyclohexylamine

Example 15

A 50% strength by weight solution of 4-tert-butylphenol in n-butanol was prepared. This solution was subsequently passed together with hydrogen at 180° C. and a total pressure of 200 bar through a flow-through reactor charged with 1.2 l of the Ru catalyst C (5% of Ru on SiO$_2$ extrudates). The amount of phenol fed continuously into the reactor corresponded to a WHSV of 0.55 kg/l×h. After the solvent had been distilled off, the hydrogenation product had the following composition:

99.9% of cis,trans-4-tert-butylcyclohexanol 0.1% of tert-butylcyclohexane

Example 16

3 g of catalyst A (3% Ru/SiO$_2$) were placed in a 300 ml pressure reactor. The reactor was subsequently charged with 150 ml of a 33% strength solution of i-butyraldehyde in THF. The hydrogenation was carried out at 130° C. and a pressure of 250 bar using pure hydrogen. The hydrogenation was continued until no more hydrogen was taken up and the reactor was subsequently vented. After distilling off the solvent, the reaction product was analyzed by gas chromatography. i-Butyraldehyde had been reacted completely. 99.7% of i-butanol were obtained.

Example 17

3 g of catalyst A (3% Ru/SiO$_2$) were placed in a 300 ml pressure reactor. The reactor was subsequently charged with 150 ml of a 33% strength solution of 2-ethylhexanal in THF. The hydrogenation was carried out at 130° C. and a pressure of 250 bar using pure hydrogen. The hydrogenation was continued until no more hydrogen was taken up and the reactor was subsequently vented. After distilling off the solvent, the reaction product was analyzed by gas chromatography. 2-Ethylhexanal had been reacted completely. 99.5% of ethylhexanol were obtained.

Example 18

3 g of catalyst A (3% Ru/SiO$_2$) were placed in a 300 ml pressure reactor. The reactor was subsequently charged with 150 ml of a 33% strength solution of benzaldehyde in THF. The hydrogenation was carried out at 130° C. and a pressure of 250 bar using pure hydrogen. The hydrogenation was continued until no more hydrogen was taken up and the reactor was subsequently vented. After distilling off the solvent, the reaction product was analyzed by gas chromatography. Benzaldehyde had been reacted completely. 98.5% of cyclohexylmethanol were obtained.

Example 19

2 g of Ru catalyst A (3% Ru/SiO$_2$) were placed in a 300 ml pressure reactor and admixed with 160 g (0.33 mol) of a 30% strength solution of 2,5-dimethylhexynediol in isopropanol. The hydrogenation was carried out at 130° C. and a pressure of 30 bar using pure hydrogen. The hydrogenation was continued until no more hydrogen was taken up and the reactor was subsequently vented. The conversion of the alkynol was 100%. The yield of 2,5-dimethylhexanediol was 98.5%.

Example 20

2 g of catalyst B (5% Ru/SiO$_2$) were placed in a 300 ml pressure reactor. The reactor was subsequently charged with 150 ml of a 60% strength solution of butyronitrile in THF. The hydrogenation was carried out at 130° C. and a pressure of 40 bar using pure hydrogen. The hydrogenation was continued until no more hydrogen was taken up and the reactor was subsequently vented. After distilling off the solvent, the reaction product was analyzed by gas chromatography. It comprised 95.4% of butylamine, 0.5% of butyronitrile and 2.3% of dibutylamine.

Example 21

2 g of catalyst B (5% Ru/SiO$_2$) were placed in a 300 ml pressure reactor. The reactor was subsequently charged with 150 ml of dimethylaminopropionitrile. The hydrogenation was carried out at 120° C. and a pressure of 40 bar using pure hydrogen. The hydrogenation was continued until no more hydrogen was taken up and the reactor was subsequently vented. The reaction product was analyzed by gas chromatography. It comprised 95% of dimethylaminopropylamine and 2% of bis(dimethylaminopropyl)amine. The dimethylaminopropionitrile had been reacted completely.

Example 22

An electrically heatable flow-through reactor was charged with 1 kg of catalyst C (5% of Ru on SiO$_2$ extrudates). The hydrogenation of n-butyraldehyde was then commenced at 50 bar and 160° C. without prior activation. The hydrogenation was carried out continuously in the upflow mode, with part of the hydrogenation product being recirculated via a circulation pump and mixed with the feed upstream of the reactor. In this way, an amount of hydrogenation product corresponding to 10 times the amount of n-butyraldehyde was added as solvent. The amount of starting material fed continuously to the reactor corresponded to a WHSV of 0.55 kg/l×h. The output from the reactor no longer contained any n-butyraldehyde and the yield of n-butanol was 99.2% (determined by gas chromatography).

Example 23

Hydrogenation of Polystyrene 2 g of catalyst B (5% Ru/SiO$_2$) were placed in a 300 ml pressure reactor. The reactor was subsequently charged with 150 ml of a 10% strength solution of Polystyrol 158 K (BASF AG) in cyclohexane. The hydrogenation was carried out at 160° C. and a pressure of 250 bar using pure hydrogen. The hydrogenation was continued until no more hydrogen was taken up and the reactor was subsequently vented. After filtration off the catalyst and distilling off the solvent, the reaction product was analyzed by NMR and gel permeation chromatography. The aromatic rings of the polystyrene had been completely hydrogenated; no chain degradation had taken place.

Example 24

Hydrogenation of Kraton G 1650

200 g of catalyst B (5% Ru/SiO$_2$) were placed in a 20 l autoclave. The reactor was subsequently charged with 15 l of a 10% strength solution of Kraton G 1650 (Shell) in cyclohexane. The hydrogenation was carried out at 160° C. and a pressure of 250 bar using pure hydrogen. The hydrogenation was continued until no more hydrogen was taken up and the reactor was subsequently vented. After filtering off the catalyst and distilling off the solvent, the reaction product was analyzed by NMR and gel permeation chromatography. The aromatic rings of the Kraton G 1650 had been completely hydrogenated; no chain degradation had taken place.

Example 25

Hydrogenation of a Linear Styrene-Butadiene Block Copolymer 2 g of catalyst B (5% Ru/SiO$_2$) were placed in a 300 ml pressure reactor. The reactor was subsequently charged with 150 ml of a 15% strength solution of a styrene-butadiene block copolymer having a linear architecture in cyclohexane (this was an unsymmetrical linear styrene-butadiene block copolymer prepared by sequential anionic polymerization in cyclohexane using sec-butyllithium as initiator. The cyclohexane contained 0.5% by volume of tetrahydrofuran (THF) so that, firstly, the proportion of 1,2-vinyl units of the copolymerized butadiene was about 50% and, secondly, simultaneous addition of styrene and butadiene resulted in the two monomers being incorporated uniformly (randomly). In this example, a short styrene block which made up 12.4% by weight of the total polymer was prepared first, followed by a pure butadiene block making up a proportion of 21.7%, then a random S/B block consisting of 16.6% of butadiene and 11.5% of styrene and finally a long styrene block making up a proportion of 37.9% of the total chain. After the polymerization, the "living" chains were protonated by means of isopropanol).

The hydrogenation was carried out at 180° C. and a pressure of 250 bar using pure hydrogen. The hydrogenation was continued until no more hydrogen was taken up and the reactor was subsequently vented. After filtering off the catalyst and distilling off the solvent, the reaction product was analyzed by NMR and gel permeation chromatography. The aromatic rings of the linear styrene-butadiene block copolymer had been completely hydrogenated; no chain degradation had taken place.

Example 26

Hydrogenation of a Star-Shaped Styrene-Butadiene Block Copolymer 2 g of catalyst B (5% Ru/SiO$_2$) were placed in a 300 ml pressure reactor. The reactor was subsequently charged with 150 ml of a 15% strength solution of a styrene-butadiene block copolymer having a star-like architecture in cyclohexane (the polymerization conditions were the same as in example 25. The difference lay in the addition of initiator, monomer and chain termination agent. Firstly, a long styrene block was polymerized by addition of sec-butyllithium and styrene. Subsequently, more butyllithium was added in a ratio of 2nd addition (BuLi)/1st addition (BuLi)=3.5, i.e. 3.5 times the amount was added the second time, followed by introduction of further styrene. The second introduction of initiator resulted in formation of short blocks, while the long block continued to grow. Finally, butadiene (26% by weight) was introduced and after the polymerization was complete (conversion >>99%) coupling was carried out using epoxidized soybean oil to form star polymers having predominantly 3 and 4 branches. Corresponding to the molar ratio of the chains, determined by the ratio of the two butyllithium additions, all statistically possible combinations of long and short branches were present in the stars, with the relative proportion being able to be predicted quite accurately on the basis of a probability calculation).

The hydrogenation was carried out at 180° C. and a pressure of 250 bar using pure hydrogen. The hydrogenation was continued until no more hydrogen was taken up and the reactor was subsequently vented. After filtering off the catalyst and distilling off the solvent, the reaction product was analyzed by NMR and gel permeation chromatography. The aromatic rings of the star-shaped styrene-butadiene block copolymer had been completely hydrogenated; no chain degradation had taken place.

Example 27

An electrically heatable flow-through reactor was charged with 1 kg of catalyst C (5% of Ru on $SiO_2$ extrudates). The hydrogenation of Kraton G 1650 (10% strength solution in cyclohexane) was then commenced at 250 bar and 160° C. without prior activation. The hydrogenation was carried out continuously in the upflow mode without recirculation of liquid. The amount of starting material fed continuously to the reactor corresponded to a WHSV of 0.3 kg/l×h. Analysis of the output from the reactor after removal of the solvent indicated complete conversion; degradation of the polymer chain was not observed.

Example 28

2 g of catalyst A (3% $Ru/SiO_2$) were placed in a 300 ml pressure reactor. The reactor was subsequently charged with 100 g of diisononyl phthalate (DINP). The hydrogenation was carried out at 120° C. and a pressure of 200 bar using pure hydrogen. The hydrogenation was continued until no more hydrogen was taken up and the reactor was subsequently vented. The conversion of the diisononyl phthalate was 100%. Diisononyl cyclohexane-1,2-dicarboxylate was obtained with a selectivity of over 99%.

Example 29

Preparation of Catalysts

A defined amount of the respective support material was impregnated with the maximum amount of a solution of ruthenium(III) nitrosyl nitrate in water which could be taken up by the respective support material. The maximum amount taken up by each support material had been determined beforehand with the aid of an authentic sample. The concentration of the solution was in each case such that the desired concentration of ruthenium in the support material resulted.

The solid obtained in this way was then dried at 120° C. for 13 hours in a rotary sphere oven. The solid obtained in this way was reduced at 300° C. in a stream of hydrogen at atmospheric pressure for 4 hours in a rotary sphere oven. After cooling and blanketing with nitrogen, the catalyst was passivated by passing 5% by volume of oxygen in nitrogen over it for 120 minutes.

Catalyst A:

Catalyst A having a ruthenium content of 3% by weight on a pulverulent $SiO_2$ support was prepared using the general method. The support material used was a silica gel powder having the following specifications:
$SiO_2$ content >99.5% by weight,
specific BET surface area=168 $m^2/g$,
water uptake=0.95 ml/g,
pore volume=0.7 (determined in accordance with DIN 66134),
particle size <100 μm.

Catalyst B:

Catalyst B having a ruthenium content of 5% by weight on a pulverulent $SiO_2$ support was prepared using the general method. The support material used was a silica gel powder having the following specifications:
$SiO_2$ content >99.5% by weight,
specific BET surface area=68 $m^2/g$,
water uptake=1.04 ml/g,
particle size <63 μm.

Catalyst C:

Catalyst C having a ruthenium content of 5% by weight on $SiO_2$ extrudates as support was prepared using the general method. The support material used comprised silica gel extrudates (diameter: 4 mm, length: 2-10 mm) made from silica gel having the following specifications:
$SiO_2$ content >99.5% by weight,
specific BET surface area=168 $m^2/g$,
water uptake=0.95 ml/g,
pore volume=0.7 (determined in accordance with DIN 66134),
particle size <100 μm.

We claim:

1. A process for hydrogenating at least one organic compound by bringing the organic compound or compounds into contact with a hydrogen-containing gas in the presence of a catalyst which comprises, as active metal, ruthenium either alone or together with at least one further metal of transition group I, VII or VIII of the Periodic Table applied to a support material based on amorphous silicon dioxide, wherein the active metal is present on the support material in an atomically dispersed form or in the form of metal particles, or in atomically dispersed form and in the form of metal particles, which metal particles are present to an extent of more than 90%, based on the number of visible particles, as isolated particles having a diameter below 10 nm, and which catalyst is obtainable by:
    i) a single or multiple treatment of a support material based on amorphous silicon dioxide with a halogen-free aqueous solution of a low molecular weight ruthenium compound and subsequent drying of the treated support material at below 200° C., wherein the low molecular weight ruthenium compound is selected from the group consisting of ruthenium(III) nitrosyl nitrate, ruthenium(III) acetate and alkali metal ruthenate (IV),
    ii) reduction of the solid obtained in i) by means of hydrogen at from 100 to 350° C.,
with step ii) being carried out directly after step i), and the support based on amorphous silicon dioxide has a BET surface area in the range from 50 to 700 $m^2/g$.

2. A process as claimed in claim 1, wherein the organic compound is an unsubstituted monocyclic or polycyclic aromatic or a monocyclic or polycyclic aromatic substituted by at least one alkyl group.

3. A process as claimed in claim 2, wherein the monocyclic or polycyclic aromatic is selected from among benzene, toluene, xylenes, cumene, diphenylmethane, tribenzenes, tetrabenzenes pentabenzenes, hexabenzenes, triphenylmethane, alkyl-substituted naphthalenes, naphthalene, alkyl-substituted anthracenes, anthracene, alkylsubstituted tetralins and tetralin.

4. A process as claimed in claim 3, wherein benzene is converted into cyclohexane.

5. A process as claimed in claim 1, wherein the organic compound is an aromatic compound in which at least one hydroxyl group or at least one amino group is bound to an aromatic ring.

6. A process as claimed in claim 5, wherein the aromatic compound contains at least one substituted or unsubstituted $C_1$-$C_{10}$-alkyl group bound to an aromatic ring or at least one $C_1$-$C_{10}$-alkoxy group bound to an aromatic ring in addition to the hydroxyl group or groups or the amino group or groups.

7. A process as claimed in claim 5, wherein aniline is hydrogenated to form cyclohexylamine.

8. A process as claimed in claim 5, wherein p-tert-butylphenol, bisphenol A, 2,6-dimethylphenol or p-methylphenol is hydrogenated.

9. A process as claimed in claim 1, wherein the organic compound contains at least one C—C, C—O, N—O or C—N multiple bond.

10. A process as claimed in claim 9, wherein the organic compound containing at least one multiple bond is selected from the group consisting of aldehydes, ketones, nitriles, alkynes, alkynols, alkenes, imines, carboxylic acids, carboxylic esters and heterocyclic unsaturated compounds.

11. A process as claimed in claim 2, wherein the organic compound is a polymer containing at least one C—C double bond, at least one aromatic group or at least one carbonyl group or at least one C—N triple bond.

12. A process as claimed in claim 11, wherein the polymer is polystyrene, a butadiene copolymer or an isoprene copolymer.

13. A process as claimed in claim 11, wherein the hydrogenation is carried out in a process step which directly follows the polymerization for preparing the polymer.

14. A process as claimed in claim 1, wherein the organic compound is a benzenepolycarboxylic acid or a derivative thereof or a mixture of two or more thereof.

15. A process as claimed in claim 14, wherein the benzenepolycarboxylic acid or the derivative thereof is selected from the group consisting of monoalkyl and dialkyl esters of phthalic acid, terephthalic acid and isophthalic acid, monoalkyl, dialkyl and trialkyl esters of trimellitic acid, trimesic acid and hemimellitic acid, monoalkyl, dialkyl, trialkyl and tetraalkyl esters of pyromellitic acid, where the alkyl groups of the mentioned esters may be linear or branched and each have from 3 to 18 carbon atoms, anhydrides of phthalic acid, trimellitic acid and hemimellitic acid, pyromellitic dianhydride and mixtures of two or more thereof.

16. A process as claimed in claim 14, wherein the: benzenepolycarboxylic acid or the derivative thereof is selected from the group consisting of: di(isopentyl) phthalate having the Chemical Abstracts Registry Number (hereinafter: CAS No.) 84777-06-0; di(isoheptyl) phthalate having the CAS No. 71888-89-6; di(isononyl) phthalate having the CAS No.68515-48-0; di(isononyl) phthalate having the CAS No.28553-12-0, based on n-butene; di(isononyl) phthalate having the CAS No. 28553-12-0, based on isobutene; di(nonyl) phthalate having the CAS No. 68515-49-1; di(isodecyl) phthalate having the CAS No.68515-49-1; 1,2-di -C7-11 phthalate having the CAS No.68515-42-4; di-C7-11 phthalates having the following CAS No.: 111 381-89-6, 111 381 90-9, 111 381 91-0, 68515-44-6, 68515-45-7 and 3648-20-7; di-C9-11 phthalate having the CAS No.98515-43-5; di(isodecyl) phthalate consisting mainly of di(2-propylheptyl) phthalate; the phthalic ester containing branched or linear $C_{7-9}$-alkyl ester groups; di-$C_{7-9}$ alkyl phthalate having the CAS No.111 381-89-6; di-$C_7$-alkyl phthalate having the CAS No.68515-44-6; and di-$C_9$-alkyl phthalate having the CAS No. 68515-45-7; Jayflex DINP (CAS No. 68515-48-0), Jay-flex DIDP (CAS No.68515-49-1), PalatinoI 9-P, Vestinol 9 (CAS No.28553-12-0), TOTM-I (CAS No.3319-31-1), Linplast 68-TM, Palatinol N (CAS No.28553-12-0), Jayflex DHP (CAS No.68515-50-4), Jayflex DIOP (CAS No.27554-26-3), Jayflex UDP (CAS No.68515-47-9), Jayflex DIUP (CAS No. 85507-79-5), Jayflex DTDP (CAS No.68515-47-9), Jayflex L9P (CAS No. 68515-45-7), Jayflex L911P (CAS No.68515-43-5), Jayflex L11P (CAS No.3648-20-2), Witamol 110 (CAS No.90193-91-2), Witamol 118 (di-n-$C_8$-$C_{10}$-alkyl phthalate), Unimoll BB (CAS No.85-68-7), Linplast 1012 HP (CAS No.90193-92-3), Linplast 13 XP (CAS No.27253-26-5), Linplast 610 P (CAS No.68515-51-5), Linplast 68 FP (CAS No.68648-93-1) and Linplast 812 HP (CAS No. 70693-30-0), Palatinol AH (CAS No.117-81-7), Palatinol 711 (CAS No.68515-42-4), Palatinol 911 (CAS No.68515-43-5), Palatinol 11 (CAS No.3648-20-2), Palatinol Z (CAS No.26761-40-0) and Palatinol DIPP (CAS No.84777-06-0).

17. A process as claimed in claim 1, wherein the catalyst has at least one of the following properties:
 (1) the catalyst comprises ruthenium, either alone or together with at least one further metal of transition group I, VII or VIII of the Periodic Table, in an amount of from 0.2 to 10% by weight, based on the weight of the support;
 (2) the support material based on silicon dioxide comprises at least 90% by weight of silicon dioxide and less than 1% by weight of aluminum oxide, calculated as $Al_2O_3$.

18. A process as claimed in claim 1, wherein the catalyst contains less than 0.05% by weight of halogen, based on the total weight of the catalyst.

19. A process as claimed in claim 1, wherein the hydrogenation is carried out continuously.

20. A process as claimed in claim 1, wherein the hydrogenation is carried out at from 50 to 250° C.

21. A process as claimed in claim 1, wherein the hydrogenation is carried out in the gas phase.

22. A process as claimed in claim 1, wherein the low molecular weight ruthenium compound is ruthenium(III) nitrosyl nitrate.

23. A process as claimed in claim 1, wherein the amorphous silicon dioxide is selected from the group consisting of kieselgur, silica gels, pyrogenic silica, and precipitated silica.

24. A process as claimed in claim 23, wherein the amorphous silicon dioxide is silica gel.

\* \* \* \* \*

UNITED STATES PATENT AND TRADEMARK OFFICE
CERTIFICATE OF CORRECTION

PATENT NO. : 7,355,084 B2
APPLICATION NO. : 10/480196
DATED : April 8, 2008
INVENTOR(S) : Böttcher et al.

It is certified that error appears in the above-identified patent and that said Letters Patent is hereby corrected as shown below:

On the Title Page Item -57- in the abstract, line 7:
"amorphons silicon dioxide" should read --amorphous silicon dioxide--

In Claim 3, col. 30, indicated line 67:
"tetrabenzenes pentabenzenes" should read --tetrabenzenes, pentabenzenes--

In Claim 3, col. 31, indicated line 2:
"alkylsubstituted" should read --alkyl-substituted--

In Claim 16, col. 31, indicated line 54:
"wherein the:" should read --wherein the--

In Claim 16, col. 32, indicated lines 1 and 2:
"di(nonyl) phthalate having the CAS No. 68515–49–1;" should read
--di(nonyl) phthalate having the CAS No. 68515–46–8;--

In Claim 16, col. 32, indicated line 3:
"1,2–di–C7–11 phthalate" should read --1,2–di–$C_{7-11}$ phthalate--

In Claim 16, col. 32, indicated line 4:
"di-C7-11 phthalates" should read --di-$C_{7-11}$ phthalates--

In Claim 16, col. 32, indicated line 6:
"di-C9-11 phthalate" should read --di-$C_{9-11}$ phthalate--

UNITED STATES PATENT AND TRADEMARK OFFICE
CERTIFICATE OF CORRECTION

PATENT NO.       : 7,355,084 B2
APPLICATION NO.  : 10/480196
DATED            : April 8, 2008
INVENTOR(S)      : Böttcher et al.

It is certified that error appears in the above-identified patent and that said Letters Patent is hereby corrected as shown below:

In Claim 16, col. 32, indicated line 13:
    "Jay–flex" should read --Jayflex--

In Claim 16, col. 32, indicated line 14:
    "PalatinoI 9–P" should read --Palatinol 9–P--

Signed and Sealed this

Eighth Day of July, 2008

JON W. DUDAS
*Director of the United States Patent and Trademark Office*